United States Patent
Tamura et al.

(10) Patent No.: US 9,480,630 B2
(45) Date of Patent: Nov. 1, 2016

(54) CO-MODIFIED ORGANOPOLYSILOXANE, EMULSIFIER FOR WATER-IN-OIL EMULSION, EXTERNAL USE PREPARATION, AND COSMETIC COMPOSITION USING THE SAME

(71) Applicant: Dow Corning Toray Co., Ltd., Tokyo (JP)

(72) Inventors: Seiki Tamura, Ichihara (JP); Sayuri Sawayama, Ichihara (JP); Seiji Hori, Ichihara (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 0 days.

(21) Appl. No.: 14/369,236

(22) PCT Filed: Dec. 25, 2012

(86) PCT No.: PCT/JP2012/084269
§ 371 (c)(1),
(2) Date: Jun. 27, 2014

(87) PCT Pub. No.: WO2013/100169
PCT Pub. Date: Jul. 4, 2013

(65) Prior Publication Data
US 2015/0011656 A1    Jan. 8, 2015

(30) Foreign Application Priority Data
Dec. 27, 2011 (JP) .................. 2011-286975

(51) Int. Cl.
*C07F 7/18* (2006.01)
*A61K 8/06* (2006.01)
*C08G 77/38* (2006.01)
*A61K 8/893* (2006.01)
*A61Q 19/00* (2006.01)
*C08G 77/46* (2006.01)

(52) U.S. Cl.
CPC .............. *A61K 8/064* (2013.01); *A61K 8/893* (2013.01); *A61Q 19/00* (2013.01); *C08G 77/38* (2013.01); *C08G 77/46* (2013.01)

(58) Field of Classification Search
USPC .................. 556/430, 445, 449, 450
See application file for complete search history.

(56) References Cited

U.S. PATENT DOCUMENTS

| | | |
|---|---|---|
| 4,122,029 A | 10/1978 | Gee et al. |
| 4,268,499 A | 5/1981 | Keil |
| 4,381,241 A | 4/1983 | Romenesko et al. |
| 4,431,789 A | 2/1984 | Okazaki et al. |
| 4,689,383 A | 8/1987 | Riffle et al. |
| 4,698,178 A | 10/1987 | Huttinger et al. |
| 4,853,474 A | 8/1989 | Bahr et al. |
| 4,908,228 A | 3/1990 | Lo |
| 4,963,093 A | 10/1990 | Dragan |
| 5,831,080 A | 11/1998 | Sejpka et al. |
| 6,218,560 B1 | 4/2001 | Abele et al. |
| 6,784,271 B2 | 8/2004 | Nakanishi |
| 7,771,709 B2 | 8/2010 | Nakanishi et al. |
| 8,288,498 B2 | 10/2012 | Hayashi et al. |
| 8,784,787 B2 | 7/2014 | Tamura et al. |
| 2002/0131947 A1 | 9/2002 | Nakanishi |
| 2009/0062459 A1 | 3/2009 | Thum et al. |
| 2009/0203802 A1 | 8/2009 | Kamei et al. |
| 2010/0266651 A1* | 10/2010 | Czech .............. A61K 8/893 424/401 |
| 2012/0269747 A1 | 10/2012 | Iimura et al. |
| 2014/0004065 A1 | 1/2014 | Souda et al. |

FOREIGN PATENT DOCUMENTS

| | | |
|---|---|---|
| EP | 0 176 884 A2 | 4/1986 |
| EP | 0 612 759 A1 | 8/1994 |
| EP | 1 004 614 A1 | 5/2000 |
| JP | S 57-149290 A | 9/1982 |
| JP | S 62-068820 A | 3/1987 |
| JP | S 63-139106 A | 6/1988 |
| JP | H 02-228958 A | 9/1990 |
| JP | H 05-186596 A | 7/1993 |
| JP | H 06-145023 A | 5/1994 |
| JP | H 06-089147 B2 | 11/1994 |
| JP | H 08-269204 A | 10/1996 |
| JP | 2583412 B | 2/1997 |
| JP | 2613124 B | 5/1997 |
| JP | H 10-310509 A | 11/1998 |

(Continued)

OTHER PUBLICATIONS

International Search Report for Application No. PCT/JP2012/084269 dated Apr. 29, 2013, 3 pages.
International Search Report for Application No. PCT/JP2012/084285 dated Apr. 24, 2013, 3 pages.
Machine-assisted English language abstract for EP 0 176 884 extracted from espacenet.com database on Aug. 28, 2014, 1 pages.
English language abstract for EP 0 612 759 extracted from espacenet.com database on Aug. 28, 2014, 1 pages.
English language abstract for EP 1 004 614 extracted from espacenet.com database on Aug. 28, 2014, 2 pages.
English language abstract for JPS 57-149290 extracted from espacenet.com database on Aug. 28, 2014, 2 pages.

(Continued)

*Primary Examiner* — Pancham Bakshi
(74) *Attorney, Agent, or Firm* — Howard & Howard Attorneys PLLC

(57) ABSTRACT

A co-modified organopolysiloxane represented by General Formula (1): $R^2R^1{}_2SiO(R^1{}_2SiO)_nSiR^1{}_2Q$, and a surfactant/dispersing agent, emulsifier for a water-in-oil emulsion, external use preparation and cosmetic composition comprising the same. In the formula, the $R^1$ groups are monovalent hydrocarbon group having 1 to 12 carbon atoms, $R^2$ is a monovalent hydrocarbon group having 13 to 30 carbon atoms, and Q is a sugar alcohol group-containing organic group or a diglycerin derivative group having an average number of repetitions of a glycerin unit of 1.1 to 2.9, n is a number in a range of 0 to 100.

14 Claims, No Drawings

(56) References Cited

FOREIGN PATENT DOCUMENTS

| | | |
|---|---|---|
| JP | H 10-316526 A | 12/1998 |
| JP | H 10-316527 A | 12/1998 |
| JP | H 10-316536 A | 12/1998 |
| JP | H 10-316540 A | 12/1998 |
| JP | 2844453 B | 1/1999 |
| JP | 2002-179798 A | 6/2002 |
| JP | 3389311 B | 3/2003 |
| JP | 3513682 B | 3/2004 |
| JP | 2004-169015 A | 6/2004 |
| JP | 2004-231605 A | 8/2004 |
| JP | 2004-231607 A | 8/2004 |
| JP | 2004-231608 A | 8/2004 |
| JP | 2005-042097 A | 2/2005 |
| JP | 2005-089494 A | 4/2005 |
| JP | 3678420 B | 8/2005 |
| JP | 2005-232088 A | 9/2005 |
| JP | 2005-344076 A | 12/2005 |
| JP | 2006-218472 A | 8/2006 |
| JP | 2008-274241 A | 11/2008 |
| JP | 4187198 B2 | 11/2008 |
| JP | 4485134 B2 | 6/2010 |
| WO | WO 2006/127883 A2 | 11/2006 |
| WO | WO 2007/109240 A2 | 9/2007 |
| WO | WO 2008/046763 A1 | 4/2008 |
| WO | WO 2009/006091 A2 | 1/2009 |
| WO | WO 2011/028765 A1 | 3/2011 |
| WO | WO 2011/028770 A1 | 3/2011 |
| WO | WO 2011/136397 A1 | 3/2011 |
| WO | WO 2011/049246 A1 | 4/2011 |
| WO | WO 2011/049248 A1 | 4/2011 |
| WO | WO 2013/103147 A1 | 7/2013 |

OTHER PUBLICATIONS

English language abstract for JPS 62-068820 extracted from PAJ database on Aug. 28, 2014, 1 page.
English language abstract for JPS 63-139106 extracted from PAJ database on Aug. 28, 2014, 1 page.
English language abstract for JPH 02-228958 extracted from espacenet.com database on Aug. 28, 2014, 2 pages.
English language abstract and machine-assisted English translation for JPH 05-186596 extracted from the PAJ database on Aug. 28, 2014, 33 pages.
English language abstract and machine-assisted English translation for JPH 06-145023 extracted from the PAJ database on Aug. 28, 2014, 22 pages.
English language abstract for JPH 06-089147 extracted from espacenet.com database on Aug. 27, 2014, 2 pages.
English language abstract and machine-assisted English translation for JPH 08-269204 extracted from the PAJ database on Aug. 28, 2014, 29 pages.
Machine-assisted English translation for JP 2583412 extracted from the PAJ database on Aug. 28, 2014, 15 pages.
Machine-assisted English translation for JP 2613124 extracted from the PAJ database on Aug. 28, 2014, 43 pages.
English language abstract and machine-assisted English translation for JPH 10-310509 extracted from the PAJ database on Sep. 3, 2014, 22 pages.
English language abstract and machine-assisted English translation for JPH 10-316526 extracted from the PAJ database on Aug. 28, 2014, 19 pages.
English language abstract and machine-assisted English translation for JPH 10-316527 extracted from the PAJ database on Aug. 28, 2014, 20 pages.
English language abstract and machine-assisted English translation for JPH 10-316536 extracted from the PAJ database on Aug. 28, 2014, 21 pages.
English language abstract and machine-assisted English translation for JPH 10-316540 extracted from the PAJ database on Aug. 28, 2014, 21 pages.
Machine-assisted English translation for JP 2844453 extracted from the PAJ database on Aug. 27, 2014, 36 pages.
English language abstract for JP 2002-179798 extracted from espacenet.com database on Aug. 28, 2014, 2 pages.
Machine-assisted English translation for JP 3389311 extracted from the PAJ database on Aug. 27, 2014, 42 pages.
Machine-assisted English translation for JP 3513682 extracted from the PAJ database on Aug. 28, 2014, 20 pages.
English language abstract for JP 2004-169015 extracted from espacenet.com database on Aug. 28, 2014, 2 pages.
English language abstract and machine-assisted English translation for JP 2004-231605 extracted from the PAJ database on Aug. 28, 2014, 43 pages.
English language abstract and machine-assisted English translation for JP 2004-231607 extracted from the PAJ database on Aug. 28, 2014, 44 pages.
English language abstract and machine-assisted English translation for JP 2004-231608 extracted from the PAJ database on Aug. 28, 2014, 50 pages.
English language abstract for JP 2005-042097 extracted from espacenet.com database on Aug. 27, 2014, 2 pages.
English language abstract and machine-assisted English translation for JP 2005-089494 extracted from the PAJ database on Aug. 27, 2014, 30 pages.
Machine-assisted English translation for JP 3678420 extracted from the PAJ database on Aug. 28, 2014, 63 pages.
English language abstract and machine-assisted English translation for JP 2005-232088 extracted from the PAJ database on Sep. 3, 2014, 22 pages.
English language abstract and machine-assisted English translation for JP 2005-344076 extracted from the PAJ database on Aug. 27, 2014, 23 pages.
English language abstract and machine-assisted English translation for JP 2006-218472 extracted from the PAJ database on Aug. 27, 2014, 27 pages.
English language abstract for JP 2008-274241 extracted from espacenet.com database on Aug. 28, 2014, 2 pages.
English language abstract not found for JP 4187198; however, see English language equivalent U.S. Pat. No. 6,784,271. Original document extracted from esapcenet.com database on Aug. 28, 2014, 32 pages.
English language abstract and machine-assisted English translation for JP 4485134 extracted from the PAJ database on Aug. 27, 2014, 92 pages.
English language abstract for WO 2011/049246 extracted from espacenet.com database on Aug. 28, 2014, 2 pages.
English language abstract for WO 2011/049248 extracted from espacenet.com database on Aug. 28, 2014, 2 pages.
Kumano et al., "Studies of Water-In-Oil (w/o) Emulsion Stabilized with Amino Acids or Their Salts," J. Soc. Cosmet. Chem., 28, pp. 285-314 (May 1977).
Yamaguchi, "Progress on W/O Emulsification Technique", J. Soc. Cosmet. Chem., 26, pp. 229-237(1993).

\* cited by examiner

CO-MODIFIED ORGANOPOLYSILOXANE, EMULSIFIER FOR WATER-IN-OIL EMULSION, EXTERNAL USE PREPARATION, AND COSMETIC COMPOSITION USING THE SAME

CROSS-REFERENCE TO RELATED APPLICATIONS

This application is the National Stage of International Patent Application No. PCT/JP2012/084269, filed on Dec. 25, 2012, which claims priority to and all the advantages of Japanese Patent Application No. 2011-286975, filed on Dec. 27, 2011, the content of which is incorporated herein by reference.

TECHNICAL FIELD

The present invention relates to a so-called "tri-block type" co-modified organopolysiloxane which does not have an oxyalkylene structure having an average number of repetitions of an oxyalkylene unit of 2 or higher in the molecule, in which one molecular chain terminal of a straight chain polysiloxane chain is modified by a hydrophilic group that is a diglycerin derivative group or a sugar alcohol group-containing organic group and in which the other molecular chain terminal is modified by a monovalent hydrocarbon group having 13 to 30 carbon atoms, and a surfactant/dispersing agent, and especially an emulsifier for a water-in-oil emulsion, containing the same. In addition, the present invention relates to the aforementioned co-modified organopolysiloxane, a water-in-oil emulsion containing the same, and an external use preparation or cosmetic composition containing these. Furthermore, the present invention relates to a co-modified organopolysiloxane able to be designed as a completely polyoxyethylene (PEG)-free formulation without impairing the effect of improved feel brought about by a diglycerin derivative group or a non-polyether-modified silicone that is modified by a sugar alcohol group-containing organic group due to particularly excellent emulsification and dispersion properties in an oil phase, and a surfactant/dispersing agent, emulsifier for a water-in-oil emulsion, external use preparation or cosmetic composition containing the same.

BACKGROUND ART

Silicones having hydrophilic groups exhibit excellent surface activity due to possessing both a silicone moiety, which exhibits properties such as hydrophobicity, softness, lubricity and chemical stability, and a hydrophilic group moiety, which exhibits properties such as hydrophilicity, moisture retention properties and adhesive properties. Therefore, silicones having hydrophilic groups are widely used in foods, resins, coatings, cosmetic compositions and the like, and a variety of hydrophilic silicone compounds have been known in the past. In particular, silicone oils such as low molecular weight cyclic siloxanes are often blended in order to improve the sensation during use of a cosmetic composition, and polyether-modified silicones (polyether modified polysiloxanes) are widely used as cosmetic composition raw materials such as surfactants due to exhibiting good compatibility with silicone oils.

In the field of cosmetic products, emulsifiers for water-in-oil emulsions is the use in which the value of polyether-modified silicones is maximized. Water-in-oil emulsion systems exhibit better moisture resistance than oil-in-water emulsions and have the characteristic of being able to maintain an effect such as cosmetic retainability. However, stabilizing water-in-oil emulsions has historically been more difficult than stabilizing oil-in-water emulsions, and until about 30 years ago, the only method for stabilizing water-in-oil emulsions was by solidifying an oil phase (external phase) with a wax (a beeswax-Borax-based emulsifier), which led to poor usability and sensation during use as a cosmetic product. In addition, this technique involved problems such as difficulty in maintaining stability in regions having wide temperature variations and difficulty in adjusting the feeling to touch by altering the oil phase/aqueous phase ratio.

After this, an amino acid gel emulsification method (Non-Patent Document 1) and a high internal phase W/O emulsion using this method were developed in 1977, and a breakthrough was achieved by ameliorating the oily sensation during use by being able to reduce the quantity of the oil phase and gelling the oil phase by means of a lamellar structure obtained by arranging an amino acid and a surfactant in a regular manner, thereby improving the stability of the emulsion. Furthermore, a method for obtaining a stable W/O emulsion by adding an aqueous phase to an oily gel obtained by using a clay mineral that was hydrophobized/oil-swelled by means of a quaternary ammonium salt-based organic cation and the like (Non-Patent Document 2) was developed, and this contributed to broadening the scope of formulations according to the texture and feeling to touch of a water-in-oil emulsion cosmetic composition. However, these conventional W/O emulsion stabilization techniques were developed in order to maintain the stability of a system by gelling or solidifying an oil phase (external phase), meaning that it was difficult to stabilize an emulsion while maintaining a low emulsion viscosity.

With a technique for producing a W/O emulsion having excellent stability while having a low viscosity and good fluidity, it would be possible to obtain a practical W/O emulsion cosmetic composition having a soft feeling to touch, light smoothness and good spreadability. That is, by using this technique in a combination with conventional formulation techniques for obtaining a stable cream, it is possible to freely adjust the texture or feeling to touch of a cosmetic composition according to consumers' wishes and the intended use of the cosmetic composition, and such a composition was thought to be of high value. Therefore, attempts were made to improve the feeling to touch by using the aforementioned techniques in a formulation obtained by adding a silicone oil to an oil phase. However, it is not possible to stably gel a silicone oil by using the aforementioned techniques, and it was not possible to obtain a W/O emulsion cosmetic composition having excellent stability and feeling to touch.

Under such circumstances, attention was focused purely on emulsification performance, not hardening oils, and research into the use of polyether-modified silicones in emulsifiers for water-in-oil emulsions was carried out, mainly in the USA and Europe (Patent Documents 1 to 5). Until around 1985, polyether-modified dimethylpolysiloxanes functioned as useful emulsifiers for oil phases that primarily contain silicone oils, long chain alkyl/polyether-comodified dimethylpolysiloxanes functioned as useful emulsifiers for oil phases that primarily contain organic oils or mixed oils of silicone oils and organic oils, and these were confirmed as having the previously unachievable property of obtaining a W/O emulsion cosmetic composition having both more excellent stability and lower viscosity than previous compositions.

Thereafter, organic emulsifiers that produced water-in-oil emulsions having low viscosity and excellent stability, such as polyglyceryl polyhydroxystearates and isostearyl glyceryl, were developed, but these materials do not have a silicone moiety in the structure, and therefore have the problem of being unable to obtain a stable emulsion in formulations in which the proportion of a silicone oil in an oil phase is high. In addition, these materials are inferior to polyether-modified silicones in terms of feeling to touch. Therefore, these emulsifiers for organic W/O emulsions are often used in combination with polyether-modified silicones in, for example, formulations in which the proportion of a silicone oil in an oil phase is high.

This is one reason why polyether-modified silicones currently occupy an important position in the field of emulsifiers for water-in-oil emulsions used in cosmetic products.

Meanwhile, glycerin-modified silicones have long been known as non-ionic hydrophilic silicones that differ from polyether-modified silicones (Patent Documents 6 to 19), and investigations into the use of these in cosmetic compositions have increased. However, stable production of glycerin-modified silicones is extremely difficult technically, and unsaturated group-containing glycerin derivatives, which are raw materials of glycerin-modified silicones, are expensive and are difficult to procure on an industrial scale. As a result, the number of commercially available glycerin-modified silicone products is far lower than that of polyether-modified silicones, and because these are also expensive, actual use of glycerin-modified silicones has been limited.

Recently, it has been thought that glycerin-modified silicone was superior to polyether-modified silicone from the perspective of oxidation stability and, thus, glycerin-modified silicone has attracted attention as a surfactant having greater safety. For example, in Germany, a demand for the replacement of raw materials having polyether groups with non-polyether raw materials has increased due to a negative perception of the safety of products comprising polyoxyethylene (PEG) due to testing done by a consumer information magazine company. Moreover, in South Korea, increased interest in non-polyether silicone surfactants has emerged due to a concern that products containing polyoxyethylene (PEG) may irritate the skin because formalin may be produced as a result of oxidation degradation of PEG.

In light of the above, there is a global trend toward changing the entire formulation of end consumer products such as cosmetic products, and the like, to PEG-FREE formulations. In concord with this trend, there is a demand for progression from the old polyether-modified silicone technology to non-polyether hydrophilic silicone in the field of silicone-based surfactants as well. However, as well as being expensive, conventional glycerin-modified silicones have significant problems in that they do not appear in patent document searches. This is because even if a glycerin-modified silicone is used as an emulsifier for a water-in-oil emulsion, it cannot be used in an actual formulation because performance is low. As a result, there is no choice but to use a more reliable polyether-modified silicone emulsifier in combination with the glycerin-modified silicone, which makes it impossible to achieve the goal of shifting all cosmetic compositions to PEG-FREE formulations.

More specifically, an undecyl glyceryl ether-modified organopolysiloxane that is disclosed in Patent Document 11 can form a stable W/O emulsion if the oil phase is a silicone oil, but cannot form a stable emulsion in formulations in which an oil phase is a mixed system of an organic oil and a silicone oil or an oil phase primarily contains an organic oil. Therefore, an undecyl glyceryl ether-modified organopolysiloxane cannot be used alone as an emulsifier in this type of formulation, and it is essential for the formulation to be aided by an organic emulsifier or a long chain alkyl/polyether-comodified dimethylpolysiloxane.

In addition, the polyhydric alcohol-modified silicone disclosed in Patent Document 14 is characterized by having a linear siloxane branch as a lipophilic group in the structure, and types having a triglycerol group as a hydrophilic group and a medium chain alkyl group as an optional secondary lipophilic group are commercially available. By having two lipophilic groups in the structure, this material can be used in a wider range of oil agents than the material disclosed in Patent Document 11. Specifically, it is possible to form a stable W/O emulsion with a silicone oil, an ester oil in which the alkyl chain length is not long, a triglyceride, or a mixed oil comprising a silicone oil and a variety of organic oils. However, in cases where the oil phase comprises a non-polar organic oil such as a mineral oil and isododecane or in the case of a mixed oil system in which the proportion of these non-polar oils is high, it is not possible to reduce the emulsion particle diameter due to emulsification performance being poor, particles agglomerate over time or when subjected to heat, and the emulsion separates. As a result, this polyhydric alcohol-modified silicone cannot be used alone as an emulsifier in this type of formulation, and it is essential for the formulation to be aided by an oil-gelling agent such as an organic emulsifier, a long chain alkyl/polyether-comodified dimethylpolysiloxane and a clay mineral that has been hydrophobized/oil-swelled by means of a quaternary ammonium salt-based organic cation and the like.

The branched polyglycerol-modified silicone disclosed in Patent Document 15 is produced by addition/graft polymerizing 2,3-epoxy-1-propanol with a silicone having one or more functional group selected from among the group comprising a hydroxy group, a carboxy group, an amino group, an imino group, a mercapto group and an epoxy group in the presence of an acidic or basic catalyst. However, with this method, the siloxane backbone disconnects during the graft polymerization, which results in two or more components having different properties being prone to be produced as the copolymer. This leads to a multitude of problems related to variable product quality, refining processes, and the like. Therefore, this is an extremely important material for maintaining the stability and emulsion viscosity of an oil-water mixture, that is, a material that is not suited to the functions of an emulsifier. In addition, because branched polyglycerol groups contain an extremely high number of hydroxyl groups per hydrophilic group, when modifying a silicone with said hydrophilic group, the hydrophilic/lipophilic balance (HLB) readily breaks down due to small variations in the degree of modification caused by reaction conditions or raw material considerations, meaning that the stability, viscosity or the like of the W/O emulsion varies greatly according to the branched polyglycerol-modified silicone lot. Therefore, branched polyglycerol groups exhibit an excessively strong autoagglutination force, and therefore tend to significantly increase the viscosity of a branched polyglycerol-modified silicone, meaning that compatibility between an oil phase and a modified silicone is reduced, energy transfer efficiency during mechanical emulsification is reduced, and it is extremely difficult to obtain a stable W/O emulsion having a fine particle diameter.

When explained in relation to the field of cosmetic products, the both terminal silicone-modified glycerin disclosed in Patent Documents 18 and 19 is a material that achieves excellent performance as an agent for dispersing a powder in an oil in cases where the oil phase is a silicone oil, and is a material in which the function as an emulsifier for a water-in-oil emulsion is low both inherently and in terms of being usable with a wide variety of oil agents.

Among Patent Documents 6 to 19, which relate to glycerin-modified silicones, the four technologies mentioned above are used in currently commercially available products. Therefore, it is thought that materials other than these have been judged by the applicant to exhibit insufficient value or effect to be commercialized.

With this in mind, the inventors of the present invention realized the following matters. Applications of monoglycerin-modified silicones, triglycerin-modified silicones and polyglycerin-modified silicones having many glycerin units in cosmetic compositions have been reported in many patent documents, and performance limits of these silicones as emulsifiers for water-in-oil emulsions are clear from market research. However, there has been very little research that focuses on diglycerin-modified silicones (Patent Document 13), and of the many past patent documents that relate to the use of glycerin-modified silicones other than this in cosmetic compositions, only 12 documents disclose diglycerin-modified silicones in practical examples (Patent Document 14 and Patent Documents 20 to 30). Furthermore, only Patent Documents 13 and 26 investigate diglycerin-modified silicones as emulsifiers for water-in-oil emulsions.

More specifically, in Patent Document 14, the siloxane compound 1 in the practical examples corresponds to a diglycerin-modified silicone, but only the detergent composition in Practical Example 1, the make-up remover in Practical Example 8 and the make-up remover in Practical Example 11 relate to the blending of this siloxane compound 1 in a cosmetic composition, and all three are aqueous systems that do not contain an oil component. Therefore, these documents do not investigate the use of diglycerin-modified silicones as emulsifiers for water-in-oil emulsions.

Patent Documents 20 to 24, 28 and 29 are formulations that are completely different from water-in-oil emulsions, and therefore do not mention investigations into the use of diglycerin-modified silicones in this type of use. Patent Document 25 relates to a method for refining a modified silicone compound having a branched polymer comprising a hydrophilic group, and only discloses a method for producing a deodorized diglycerin-modified silicone in Practical Example 5 and preparing a non-aqueous oil-based foundation using this deodorized diglycerin-modified silicone in Practical Example 14. Therefore, these documents do not investigate the use of diglycerin-modified silicones as emulsifiers for water-in-oil emulsions. In addition, Patent Document 30 discloses a technique for providing a cosmetic composition containing a silicone oil-containing oil agent and having excellent emulsion stability, but only discloses a diglycerin-modified silicone in Synthesis Example 5, and does not disclose a practical example in which this diglycerin-modified silicone is actually blended in a cosmetic composition.

Patent Document 26 relates to a cosmetic composition that is characterized by containing a clay mineral and the polyhydric alcohol-modified silicone disclosed in Patent Document 14, and Production Example 6 discloses a diglycerin-modified silicone having a specific structure. In addition, Practical Example 14 discloses a water-in-oil cream that contains this diglycerin-modified silicone and dimethyldistearyl ammonium hectorite. However, because the viscosity of the emulsion is too low when the diglycerin-modified silicone of Production Example 6 is used as an emulsifier, stability cannot be maintained unless the oil phase is thickened by means of the clay mineral. In addition, this diglycerin-modified silicone has poor compatibility with a variety of organic oils, and even if the clay mineral is additionally used in a formulation in which the proportion an organic oil in the oil phase is high, the stability of the emulsion cannot be maintained.

Patent Document 27 is an invention that relates to a powder composition and powder-in-oil dispersion comprising a powder and/or a coloring agent and, of the polyhydric alcohol-modified silicones disclosed in Patent Document 14, a polyglycerin-modified silicone having a linear siloxane branch, and also relates to a cosmetic composition containing these, and Production Example 1 discloses a diglycerin-modified silicone having a specific structure. Practical Example 1 discloses a powder-in-oil dispersion, Practical Example 5 discloses a powder composition, Practical Examples 9 and 13 disclose sunscreen agents, Practical Example 17 discloses an oil-in-water cream, Practical Example 21 discloses a water-in-oil cream, Practical Example 23 discloses a foundation, Practical Example 29 discloses an eye liner, Practical Examples 37 and 38 disclose a sun-screening milky lotion, Practical Example 40 discloses an O/W sun-screening milky lotion, and these contain this diglycerin-modified silicone. However, in all of these water-in-oil emulsion-based formulations (Practical Examples 9, 13, 21, 23, 29, 37 and 38), the diglycerin-modified silicone is used as a powder dispersing agent or an agent for treating the surface of a powder, and a polyether-modified silicone and/or a crosslinked polyether-modified silicone is used as an emulsifier for a water-in-oil emulsion in all of these examples. Therefore, these documents do not investigate the use of diglycerin-modified silicones as emulsifiers for water-in-oil emulsions. Furthermore, this diglycerin-modified silicone has poor compatibility with a variety of organic oils, and it is not possible to obtain a stable powder-in-oil dispersion in a formulation in which the proportion of an organic oil in the oil phase is high.

Patent Document 13 discloses a glyceryl ether-modified organo(poly)siloxane having a specific structure, a method for producing same, and a cosmetic composition containing the same, and Practical Examples 2, 4, 6 and 8 disclose compounds corresponding to diglycerin-modified silicones and methods for producing same. In addition, the results of an emulsification test (water-in-oil emulsion) of a simple formulation comprising the compound of Practical Example 2, a silicone oil and water are reported in Experimental Example 1, and the results obtained by blending the compound of Practical Example 2 in a hair rinse (aqueous system) having a specific composition are reported in Cosmetic Composition Formulation Example 1. However, the diglycerin-modified silicones disclosed in Practical Examples 2, 4, 6 and 8 exhibit poor compatibility with a variety of organic oils, and it is not possible to obtain a stable W/O emulsion in a formulation in which the proportion of an organic oil in the oil phase is high, meaning that separation occurs over time or when subjected to heat. Therefore, a diglycerin-modified silicone cannot be used alone as an emulsifier in this type of formulation, and it is essential for the formulation to be aided by an organic emulsifier or a long chain alkyl/polyether-comodified dimethylpolysiloxane.

In Patent Document 31, the applicant of the present application proposes the use of a co-modified organopolysiloxane copolymer having a group that has a carbosiloxane dendron structure and a hydrophilic group such as glycerin and a polyhydric alcohol in the molecule as a surfactant, powder treatment agent or surface treatment agent able to be advantageously used in the field of cosmetic compositions. In Practical Example 13 in particular, the applicant of the present application proposes a novel glycerin derivative-modified silicone No. 13 having a group that has a siloxane dendron structure, a tetraglycerin derivative group and a diglycerin derivative in the molecule, and also proposes a water-in-oil emulsion composition containing these (Formulation Example 5) and a W/O emulsion type skin external use preparation (Formulation Example 33). The glycerin derivative-modified silicone proposed here can be used to prepare a stable water-in-oil emulsion when the oil phase is a mixed system of a silicone oil and an organic oil or an oil phase primarily contains an organic oil, and has excellent feeling to touch as a cosmetic composition, but emulsification per se is difficult in a system in which a non-polar organic oil having a relatively high molecular weight, such as a mineral oil, is the primary component of the oil phase, and the emulsion stability, and especially long term emulsion stability at high temperatures, of this system has room for improvement.

Meanwhile, sugar-modified silicones have long been known as non-polyether hydrophilic silicones other than glycerin derivatives (Patent Documents 32 to 41), and many investigations have been made into the use of these sugar-modified silicones in cosmetic compositions. However, the sugar-modified silicones used in Patent Documents 32 to 36 are obtained by using amino-modified silicones as raw materials, and therefore contain nitrogen atoms in the structure. Therefore, when blended in cosmetic compositions, there are concerns regarding the possibility discoloration or the generation of unpleasant odors over time due to heat and light and the possibility of skin irritation depending on the added quantity of the sugar-modified silicone, and adequate safety checks need to be carried out when expanding the use of these sugar-modified silicones to encompass external use preparations and the like. Furthermore, problems such as controlling the rate of reaction between amino groups and sugars to a certain extent, that is, difficulty in stabilizing emulsification performance, occur.

In Patent Documents 37 to 40, the structure of the sugar moiety contains unstable acetal bonds, such as glycoside groups and glycosyl groups. Therefore, when blended in a cosmetic composition and the like, the composition is susceptible to moisture, heat and mildly acidic substances and structural changes readily occur. With regard to sugar-modified silicones, the products used in Patent Documents 37 and 39 have been commercialized as cosmetic raw materials, but these contain a polyoxyethylene (PEG) moiety in the structure. Therefore, because these materials cannot be called non-polyether hydrophilic silicones, it was not possible to achieve the goal of shifting all cosmetic compositions to PEG-FREE formulations.

In recent years, attention has been focused on sugar alcohols that are sugar reductants in order to reduce the instability inherent in so-called sugar structures such as those mentioned above, and the use of a sugar alcohol as a silicone-modified material has been newly proposed (Patent Document 41). However, this material can form a stable W/O emulsion when the oil phase is a silicone oil, but it is not possible to obtain a stable emulsion in a formulation in which the oil phase is a mixed system of an organic oil and a silicone oil or an oil phase primarily contains an organic oil. Therefore, a sugar alcohol cannot be used alone as an emulsifier in this type of formulation, it is essential for the formulation to be aided by an organic emulsifier or a long chain alkyl/polyether-comodified dimethylpolysiloxane, and there is still room for improvement in terms of performance as an emulsifier for a water-in-oil emulsion.

In Patent Document 42, the applicant of the present application proposes the use of a novel co-modified organopolysiloxane having a hydrocarbon group having 9 to 30 carbon atoms and a sugar alcohol group-containing organic group in the molecule as a surfactant, powder treatment agent or surface treatment agent able to be advantageously used in the field of cosmetic compositions. In Practical Example 1 and Practical Example 2 in particular, the applicants of the present application propose novel co-modified silicones having an alkyl group having 10 carbon atoms in a side chain and a xylitol-modified group, and also propose the ability to prepare a water-in-oil emulsion composition which contain these co-modified silicones, which contain a silicone oil and an organic oil, which has excellent feeling to touch as a cosmetic composition and which is stable for 1 month at 40° C. (Practical Examples 3 to 11 and other practical examples in Patent Document 42). In addition, it is found from the results of comparison tests that these co-modified organopolysiloxanes exhibit superior emulsion stability and feeling to touch to a polyglycerin-modified silicone having a tetraglycerin glycerin derivative group or a conventional xylitol-modified silicone that does not contain a hydrocarbon group having 9 to 30 carbon atoms.

However, the co-modified organopolysiloxane proposed by the applicant of the present application in Patent Document 42 exhibits practical emulsification/dispersion properties as a non-polyether-based modified silicone and exhibits an excellent feeling to touch improvement effect as a cosmetic composition, but when compared with the emulsification/dispersion properties of a polyether-modified silicone, there is still room for improvement in terms of emulsion stability, and especially long term stability at high temperatures. As a result, an emulsifier having a polyoxyalkylene structure is sometimes additionally used, thereby causing drawbacks in terms of feeling to touch and abandoning PEG-FREE formulations, depending on the emulsion formulation, and further improvements in emulsification/dispersion properties were desired while maintaining the excellent feeling to touch improvement effect.

In Patent Document 43, the applicant of the present application proposes an organopolysiloxane copolymer which exhibits superior feeling to touch improvement properties and compounding stability in a cosmetic product to a conventional polyether-modified silicone or silicone-based alternating copolymer (block copolymer) having a polyoxyalkylene structure in the molecule and which has, at the terminals of a straight chain polysiloxane, a group having a carbosiloxane dendron structure and a hydrophilic group (a hydrophilic segment such as a polyglycerin derivative group and a sugar alcohol group-containing organic group) as a surfactant able to be used in combination with a wide range of components blended in cosmetic compositions. Practical Example 4 in particular explicitly discloses an organopolysiloxane copolymer P4 having a group having a carbosiloxane dendron structure and a diglycerin derivative group. However, the organopolysiloxane copolymer disclosed in Patent Document 43 does not necessarily achieve excellent performance in terms of emulsification performance, including the range of applicable oil agents, but exhibits excellent powder dispersing properties. In addition, the organopolysiloxane copolymer disclosed in Patent Document 43 exhibits good powder dispersing properties for silicone oil-based oil agents, but in the case of organic oil-based oil phase, long term dispersibility in an oil phase can be insufficient depending on the type of oil agent, and there is further room for improvement.

As mentioned above, reports into investigations into the use of non-polyether-based modified silicones as emulsifiers for water-in-oil emulsions exist, but almost none are at a truly useful level, and only non-polyether-based modified silicones having the limited structures has been investigated so far. In addition, when compared with ordinary polyether-modified silicones (polyether-based hydrophilic silicone emulsifiers), no non-polyether-based modified silicones having sufficient emulsification performance with a wide range of oil agents are known as emulsifiers for water-in-oil emulsions. As a result, glycerin-modified silicones and sugar-modified silicones, which have a better feeling to touch than polyether-modified silicones and which do not suffer from oxidative degradation due to not having a polyoxyethylene (PEG) structure, could not produce a water-in-oil emulsion cosmetic composition having sufficient stability without additionally using a non-ionic surfactant such as another hydrophilic silicone emulsifier having a PEG structure and the like, and could not achieve the objectives of sufficiently exhibiting a feeling to touch improvement effect as an overall formulation and shifting the entire formulation of a cosmetic composition to a PEG-FREE formulation (i.e. a formulation that does not comprise compounds having polyoxyethylene (PEG) structures).

PRIOR ART DOCUMENTS

Non-Patent Documents

Non-Patent Document 1: Y. Kumano, J. Soc. Cosmet. Chem. January, 28, 285 (1977)
Non-Patent Document 2: Michihiro Yamaguchi, J. Soc. Cosmet. Chem. January, 26, 229 (1993)

Patent Documents

Patent Document 1: U.S. Pat. No. 4,122,029
Patent Document 2: U.S. Pat. No. 4,268,499
Patent Document 3: U.S. Pat. No. 4,381,241
Patent Document 4: U.S. Pat. No. 4,853,474
Patent Document 5: European Patent No. 176884
Patent Document 6: Japanese Examined Patent Application Publication No. S-62-34039 (Japanese Unexamined Patent Application Publication No. S-57-149290)
Patent Document 7: Japanese Patent No. 2583412 (Japanese Unexamined Patent Application Publication No. S-62-195389)
Patent Document 8: U.S. Pat. No. 4,689,383
Patent Document 9: U.S. Pat. No. 4,908,228
Patent Document 10: Japanese Examined Patent Application Publication No. H-06-089147 (Japanese Patent No. 1956013)
Patent Document 11: Japanese Patent No. 2613124 (Japanese Unexamined Patent Application Publication No. H-04-188795)
Patent Document 12: Japanese Patent No. 2844453 (Japanese Unexamined Patent Application Publication No. H-02-228958)
Patent Document 13: Japanese Patent No. 3389311 (Japanese Unexamined Patent Application Publication No. H-07-238170)
Patent Document 14: Japanese Patent No. 3976226 (Japanese Unexamined Patent Application Publication No. 2002-179798)
Patent Document 15: Japanese Patent No. 4485134 (Japanese Unexamined Patent Application Publication No. 2004-339244)
Patent Document 16: Japanese Unexamined Patent Application Publication No. 2005-042097A
Patent Document 17: Japanese Unexamined Patent Application Publication No. 2005-089494A
Patent Document 18: Japanese Unexamined Patent Application Publication No. 2005-344076A
Patent Document 19: Japanese Unexamined Patent Application Publication No. 2006-218472A
Patent Document 20: Japanese Patent No. 3513682 (Japanese Unexamined Patent Application Publication No. H-09-71504)
Patent Document 21: Japanese Unexamined Patent Application Publication No. H-10-316526
Patent Document 22: Japanese Unexamined Patent Application Publication No. H-10-316527
Patent Document 23: Japanese Unexamined Patent Application Publication No. H-10-316536
Patent Document 24: Japanese Unexamined Patent Application Publication No. H-10-316540
Patent Document 25: Japanese Patent No. 4187198 (WO2002/055588)
Patent Document 26: Japanese Patent No. 3678420 (WO2003/041664)
Patent Document 27: Japanese Unexamined Patent Application Publication No. 2004-169015A
Patent Document 28: Japanese Unexamined Patent Application Publication No. 2004-231605A
Patent Document 29: Japanese Unexamined Patent Application Publication No. 2004-231607A
Patent Document 30: Japanese Unexamined Patent Application Publication No. 2004-231608A
Patent Document 31: WO2011/049248
Patent Document 32: Japanese Unexamined Patent Application Publication No. S-62-068820A
Patent Document 33: Japanese Unexamined Patent Application Publication No. S-63-139106A
Patent Document 34: Japanese Unexamined Patent Application Publication No. H-08-269204A
Patent Document 35: WO2006/127883
Patent Document 36: WO2008/046763
Patent Document 37: Japanese Unexamined Patent Application Publication No. H-05-186596A
Patent Document 38: Japanese Unexamined Patent Application Publication No. H-06-145023
Patent Document 39: European Patent No. 612759
Patent Document 40: European Patent No. 1004614
Patent Document 41: Japanese Unexamined Patent Application Publication No. 2008-274241A
Patent Document 42: WO2011/136397
Patent Document 43: WO2011/049246

SUMMARY OF INVENTION

Technical Problems

A first objective of the present invention is to solve the above-mentioned problems and provide a co-modified organopolysiloxane that exhibits particularly excellent emulsification/dispersion properties, especially in cases where the oil phase is the continuous phase. In particular, the first objective of the present invention is to provide a co-modified organopolysiloxane which can finely and stably disperse or emulsify an aqueous phase or powder, thereby producing a composition having excellent stability over time or when subjected to heat, not only in cases where the oil phase is a silicone oil, ester oil or triglyceride, but also in cases where the oil phase is a mineral oil or isododecane, which was difficult with conventional glycerin-modified silicones.

In addition, a second objective of the present invention is to provide an emulsifier for a water-in-oil emulsion, which contains a co-modified organopolysiloxane, which can substantially ameliorate problems caused by oxidative degradation of polyoxyethylene (PEG) due to being able to be designed as a formulation that does not contain a compound having a polyoxyethylene (PEG) structure in a W/O emulsion that contains a variety of oil agents due to exhibiting particularly excellent emulsification performance when the co-modified organopolysiloxane is used alone, which can maximize the feeling to touch improvement effect of a W/O emulsion achieved by using the co-modified organopolysiloxane. As a result, a W/O emulsion type external use preparation or cosmetic composition having a soft and natural feeling to touch, light smoothness, good spreadability and good moisture retention can be produced.

Furthermore, a third objective of the present invention is to provide a surfactant or dispersing agent which can produce a stable composition (a water-in-oil emulsion composition, powder-in-oil dispersion and the like) in which a wide variety of oil agents is the continuous phase due to being a co-modified organopolysiloxane having excellent compatibility with a variety of oil agents and emulsification/dispersion properties in an oil agent.

Furthermore, a fourth objective of the present invention is to provide a water-in-oil emulsion composition that contains this type of co-modified organopolysiloxane.

Furthermore, a fifth objective of the present invention is to provide an external use preparation or cosmetic composition that contains this type of co-modified organopolysiloxane. More specifically, the fifth objective of the present invention is to provide an external use preparation or cosmetic composition which is characterized by not containing a compound containing a polyoxyethylene group or polyoxyethylene moiety, which has excellent feeling to touch due to containing the co-modified organopolysiloxane according to the present invention and which is line with the global trend of improving the constitution of an end consumer product such as a cosmetic product to a completely PEG-FREE formulation.

Solution to Problems

As a result of diligent research, the inventors of the present invention found that the above-mentioned first problem could be solved by means of a co-modified organopolysiloxane which is represented by General Formula (1) below and which does not contain an oxyalkylene structure having an average number of repetitions of an oxyalkylene unit of 2 or higher in the molecule, and thereby completed the present invention.

General Formula (1):

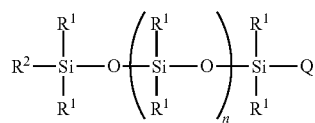

(1)

(In the formula, the $R^1$ groups are each independently a substituted or unsubstituted monovalent hydrocarbon group having 1 to 12 carbon atoms (excluding a group having an oxyalkylene structure having an average number of repetitions of an oxyalkylene unit of 2 or higher), $R^2$ is a substituted or unsubstituted monovalent hydrocarbon group having 13 to 30 carbon atoms (excluding a group having an oxyalkylene structure having an average number of repetitions of an oxyalkylene unit of 2 or higher), and Q is a sugar alcohol group-containing organic group (excluding a group having an oxyalkylene structure having an average number of repetitions of an oxyalkylene unit of 2 or higher) or a glycerin derivative group having an average number of repetitions of a glycerin unit of 1.1 to 2.9 (excluding a group having an oxyalkylene structure having an average number of repetitions of an oxyalkylene unit of 2 or higher).

n is a number in a range of 0 to 100.

In addition, the inventors of the present invention found that it was possible to solve the above-mentioned second to fourth problems by means of a surfactant or dispersing agent that contains said co-modified organopolysiloxane, and especially an emulsifier for a water-in-oil emulsion and a water-in-oil emulsion composition, and thereby completed the present invention. Furthermore, the inventors of the present invention found that it was possible to solve the above-mentioned fifth problem by means of an external use preparation or cosmetic composition which contains these co-modified organopolysiloxanes and the like which preferably does not contain a compound having a polyoxyalkylene structure, and thereby completed the present invention.

In addition, the inventors of the present invention found that the above-mentioned problems could be solved more efficiently by means of a co-modified organopolysiloxane wherein, in the above-mentioned General Formula (1), Q is a diglycerin derivative group-containing organic group (excluding a group having an oxyalkylene structure having an average number of repetitions of an oxyalkylene unit of 2 or higher) which contains 1.5 to 2.4 repeating units of one or more types of glycerin unit selected from among the sugar alcohol group-containing organic groups represented by Structural Formulae (3-1) to (3-2) below and the glycerin units represented by Structural Formulae (4-1) to (4-3) below and which is bonded to a silicon atom via a linking group that is at least divalent (excluding a group having an oxyalkylene structure having an average number of repetitions of an oxyalkylene unit of 2 or higher), and thereby completed the present invention.

Structural Formulae (3-1) to (3-2):

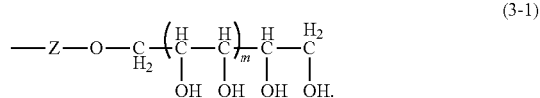

(3-1)

(In the formula, Z is a divalent organic group (excluding a group having an oxyalkylene structure having an average number of repetitions of an oxyalkylene unit of 2 or higher), and m is 1 or 2)

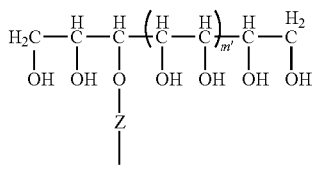
(3-2)

(In the formula, Z is synonymous with that described above, and m' is 0 or 1)

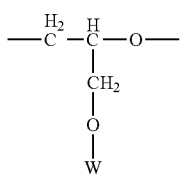
(4-1)

(In this formula, W is a hydrogen atom or an alkyl group having from 1 to 20 carbon atoms)

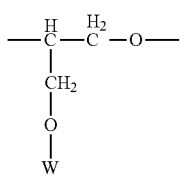
(4-2)

(In this formula, W is synonymous with the group described above).

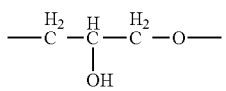
(4-3)

That is, the above-mentioned objectives can be achieved by:

[1] A co-modified organopolysiloxane which is represented by General Formula (1) below and which does not contain an oxyalkylene structure having an average number of repetitions of an oxyalkylene unit of 2 or higher in the molecule.

General Formula (1):

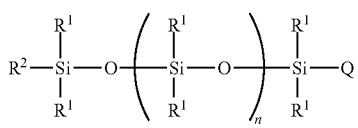
(1)

(In the formula, the $R^1$ groups are each independently a substituted or unsubstituted monovalent hydrocarbon group having 1 to 12 carbon atoms (excluding a group having an oxyalkylene structure having an average number of repetitions of an oxyalkylene unit of 2 or higher), $R^2$ is a substituted or unsubstituted monovalent hydrocarbon group having 13 to 30 carbon atoms (excluding a group having an oxyalkylene structure having an average number of repetitions of an oxyalkylene unit of 2 or higher), and Q is a sugar alcohol group-containing organic group (excluding a group having an oxyalkylene structure having an average number of repetitions of an oxyalkylene unit of 2 or higher) or a glycerin derivative group having an average number of repetitions of a glycerin unit of 1.1 to 2.9 (excluding a group having an oxyalkylene structure having an average number of repetitions of an oxyalkylene unit of 2 or higher).

n is a number in a range of 0 to 100.

[2] The co-modified organopolysiloxane described in [1], wherein, in the above-mentioned General Formula (1), Q is a diglycerin derivative group-containing organic group (excluding a group having an oxyalkylene structure having an average number of repetitions of an oxyalkylene unit of 2 or higher) which contains 1.5 to 2.4 repeating units of one or more types of glycerin unit selected from among the sugar alcohol group-containing organic groups represented by Structural Formulae (3-1) to (3-2) below and the glycerin units represented by Structural Formulae (4-1) to (4-3) below and which is bonded to a silicon atom via a linking group that is at least divalent (excluding a group having an oxyalkylene structure having an average number of repetitions of an oxyalkylene unit of 2 or higher).

Structural Formulae (3-1) to (3-2):

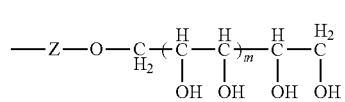
(3-1)

(In the formula, Z is a divalent organic group (excluding a group having an oxyalkylene structure having an average number of repetitions of an oxyalkylene unit of 2 or higher), and m is 1 or 2)

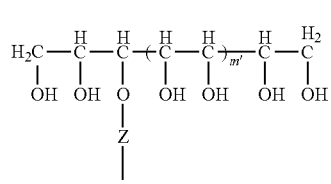
(3-2)

(In the formula, Z is synonymous with that described above, and m' is 0 or 1)

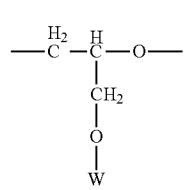
(4-1)

(In this formula, W is a hydrogen atom or an alkyl group having from 1 to 20 carbon atoms)

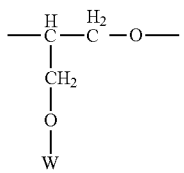

(4-2)

(In this formula, W is synonymous with the group described above).

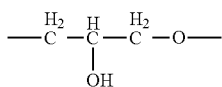

(4-3)

[3] The co-modified organopolysiloxane described in the aforementioned [1] or [2], wherein the aforementioned diglycerin derivative group-containing organic group contains a diglycerin derivative group-containing organic group represented by General Formula (5-1) below:

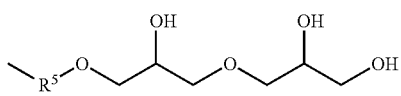

(5-1)

(In the formula, $R^5$ is a divalent organic group (excluding a group having an oxyalkylene structure having an average number of repetitions of an oxyalkylene unit of 2 or higher)) or General Formula (5-2) below:

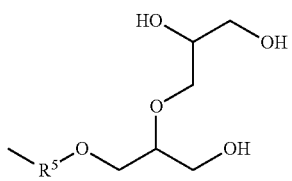

(5-2)

(wherein $R^5$ is synonymous with that described above).

[4] The co-modified organopolysiloxane described in any one of the aforementioned [1] to [3], wherein, in the above-mentioned General Formula (1), $R^1$ is a methyl group or a phenyl group, and
$R^2$ is a halogen atom-substituted or unsubstituted alkyl group having 14 to 24 carbon atoms.

[5] A surfactant or dispersing agent that contains the co-modified organopolysiloxane described in any one of the aforementioned [1] to [4].

[6] The surfactant or dispersing agent described in the aforementioned [5], which is used to prepare a composition having an oil agent as a continuous phase.

[7] The surfactant described in the aforementioned [5] or [6], which is an emulsifier for a water-in-oil emulsion.

[8] A water-in-oil emulsion composition that contains the co-modified organopolysiloxane described in any one of the aforementioned [1] to [4].

[9] A water-in-oil emulsion composition that contains (S) the co-modified organopolysiloxane described in any one of the aforementioned 1 to 4, (T) water, and (U) at least one type of oil agent that is liquid at 5 to 100° C. selected from among the group comprising silicone oils, non-polar organic compounds and lowly to highly polar organic compounds.

[10] The water-in-oil emulsion composition described in the aforementioned [8] or [9], which does not contain a compound having an oxyalkylene structure having an average number of repetitions of an oxyalkylene unit of 2 or higher.

[11] An external use preparation or cosmetic composition that contains the co-modified organopolysiloxane described in any one of the aforementioned [1] to [4].

[12] An external use preparation or cosmetic composition that contains the water-in-oil emulsion composition described in any one of the aforementioned [8] to [10].

[13] The external use preparation or cosmetic composition described in the aforementioned [11] or [12], which is in the form of a water-in-oil emulsion.

[14] The external use preparation or cosmetic composition described in any one of the aforementioned [11] to [13], which does not contain a compound having an oxyalkylene structure having an average number of repetitions of an oxyalkylene unit of 2 or higher.

Advantageous Effects of Invention

According to the present invention, it is possible to provide a tri-block type co-modified organopolysiloxane that exhibits particularly excellent emulsification/dispersion properties in cases where the oil phase is the continuous phase. In particular, the co-modified organopolysiloxane of the present invention can finely and stably emulsify/disperse an aqueous phase or powder not only in cases where the oil phase is a silicone oil, ester oil or triglyceride, but also in cases where the oil phase is a mineral oil, isododecane or the like, which was difficult with conventional glycerin-modified silicones. Therefore, the co-modified organopolysiloxane of the present invention can produce a composition having excellent stability over time or when subjected to heat, can stably emulsify/disperse an aqueous phase or powder in a wide variety of oil agent systems without using a PEG-containing compound such as a polyether-modified silicone, can obtain a composition having excellent stability over time or when subjected to heat, and can therefore improve the constitution of an end consumer product, such as an external use preparation and cosmetic product, to a completely PEG-FREE formulation, which has high environmental suitability.

By using the tri-block type co-modified organopolysiloxane of the present invention, it is possible to design a formulation that does not contain a compound having a polyoxyethylene (PEG) structure, and it is therefore possible to substantially ameliorate problems caused by oxidative degradation of polyoxyethylene (PEG) and maximize the feeling to touch improvement effect of a W/O emulsion achieved by using a diglycerin derivative-modified silicone or a sugar alcohol-modified silicone, meaning that it is possible to provide an emulsifier for a water-in-oil emulsion, which contains a co-modified organopolysiloxane and which can produce a W/O emulsion type external use preparation or cosmetic composition having a soft and natural feeling to touch, light smoothness, good spreadability and good moisture retention.

Furthermore, by using the tri-block type co-modified organopolysiloxane of the present invention, it is possible to provide a surfactant or dispersing agent that can produce a stable composition having an oil agent as the continuous phase in a wide variety of oil agent systems (a water-in-oil emulsion composition, a polyol-in-oil type emulsion composition, a polar solvent-in-oil type emulsion composition or a powder-in-oil dispersion).

Furthermore, by using the tri-block type co-modified organopolysiloxane of the present invention, it is possible to maximize the feeling to touch improvement effect of a W/O emulsion achieved by using the co-modified organopolysiloxane and provide a water-in-oil emulsion composition having excellent stability over time.

Furthermore, by using the tri-block type co-modified organopolysiloxane of the present invention, it is possible to provide an external use preparation or cosmetic composition which is characterized by not containing a compound containing a polyoxyethylene group or polyoxyethylene moiety, which has excellent feeling to touch due to containing the tri-block type co-modified organopolysiloxane according to the present invention and which is line with the global trend of improving the constitution of an end consumer product such as a cosmetic product to a completely PEG-FREE formulation.

DESCRIPTION OF THE INVENTION

Detailed explanations will now be given of the co-modified organopolysiloxane according to the present invention and use thereof as a surfactant or dispersing agent, and especially use as an emulsifier for a water-in-oil emulsion. In addition, a detailed explanation will be given of an external use preparation or cosmetic composition that contains the co-modified organopolysiloxane of the present invention, and especially an external use preparation or cosmetic composition that does not contain a compound having an oxyalkylene structure having an average number of repetitions of an oxyalkylene unit of 2 or higher. The co-modified organopolysiloxane according to the present invention has a structure in which one molecular chain terminal of a straight chain polysiloxane chain having a specific chain length is modified by a specific hydrophilic group, and in which the other molecular chain terminal is modified by a monovalent hydrocarbon group having 13 to 30 carbon atoms, and a terminally co-modified organopolysiloxane having such a structure is referred to as a "tri-block type co-modified organopolysiloxane" hereinafter.

Moreover, the tri-block type co-modified organopolysiloxane according to the present invention can be used in the same intended uses as those of the co-modified organopolysiloxane disclosed in the above-mentioned Patent Document 31 (WO 2011/049248), the co-modified organopolysiloxane disclosed in the above-mentioned Patent Document 42 (WO 2011/136397) and the organopolysiloxane copolymer disclosed in the above-mentioned Patent Document 43 (WO 2011/049246). The tri-block type co-modified organopolysiloxane according to the present invention can be used as a surfactant (emulsifier) or a variety of treatment agents (powder dispersing agent or surface treatment agent), can be used in particular as an emulsifier or a powder treatment agent or as a cosmetic raw material, can be combined with an arbitrary cosmetic raw material component, can be used in the same way as the co-modified organopolysiloxanes or organopolysiloxane copolymers disclosed in the patent documents in external use preparations, and especially in formulations, types and formulation examples of cosmetic compounds, and can be blended in a variety of cosmetic compositions. The tri-block type co-modified organopolysiloxane according to the present invention has excellent feeling to touch and, when used alone, exhibits particularly excellent capability for stably emulsifying/dispersing an aqueous phase or stably dispersing a powder in a wide variety of oil agents, and therefore forms an emulsion composition having excellent long term stability and imparts an excellent feeling to touch compared to a case in which the co-modified organopolysiloxanes and organopolysiloxane copolymers disclosed in the aforementioned patent documents are used. As a result, the present invention has the advantage of being able to provide an external use preparation or cosmetic composition which has further improved stability over time and feeling to touch and which is, if necessary, improved to a PEG-FREE formulation in the various intended uses of the co-modified organopolysiloxanes disclosed in the above-mentioned Patent Documents 31, 42 and 43.

The triblock co-modified organopolysiloxane according to the present invention is particularly superior as a surfactant, an emulsifier, or a (powder) dispersing agent, but also is effective as a tactile sensation improver, a moisturizing agent, a binder, a surface treatment agent, and a skin adhesive. Additionally, the triblock co-modified organopolysiloxane according to the present invention can be combined with water in order to function as a film agent or a viscosity adjusting agent.

The co-modified organopolysiloxane according to the present invention has a structure in which one molecular chain terminal of a straight chain polysiloxane chain having a specific chain length is modified by a specific hydrophilic group and in which the other molecular chain terminal is modified by a monovalent hydrocarbon group having 13 to 30 carbon atoms, and is more specifically the co-modified organopolysiloxane represented by General Formula (1) below.

General Formula (1):

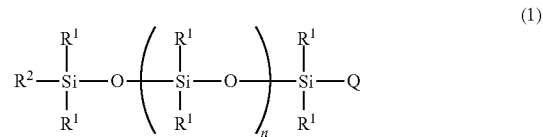

(In the formula, the $R^1$ groups are each independently a substituted or unsubstituted monovalent hydrocarbon group having 1 to 12 carbon atoms (excluding a group having an oxyalkylene structure having an average number of repetitions of an oxyalkylene unit of 2 or higher), $R^2$ is a substituted or unsubstituted monovalent hydrocarbon group having 13 to 30 carbon atoms (excluding a group having an oxyalkylene structure having an average number of repetitions of an oxyalkylene unit of 2 or higher), and Q is a sugar alcohol group-containing organic group (excluding a group having an oxyalkylene structure having an average number of repetitions of an oxyalkylene unit of 2 or higher) or a glycerin derivative group having an average number of repetitions of a glycerin unit of 1.1 to 2.9 (excluding a group having an oxyalkylene structure having an average number of repetitions of an oxyalkylene unit of 2 or higher).

n is a number in a range of 0 to 100.

Furthermore, the co-modified organopolysiloxane according to the present invention is characterized by not containing an oxyalkylene structure having an average number of repetitions of an oxyalkylene unit of 2 or higher in the molecule. It is more preferable to have only a specific sugar alcohol group-containing organic group or a glycerin derivative group having an average number of repetitions of a glycerin unit of 1.1 to 2.9 (and more preferably 1.5 to 2.4) as a hydrophilic group in the molecule, and an oxyalkylene-modified group containing an oxyalkylene structure having an average number of repetitions of an oxyalkylene unit of 2 or higher, or a group similar thereto, does not present in the molecule. If an oxyalkylene-modified group containing an oxyalkylene structure, or a structure similar thereto, is present in the molecule, it is not possible to achieve the objective of the present invention, that is, substantially improving the problem of oxidative degradation of polyoxyethylene (PEG). In addition, if a polyoxyalkylene-modified group is contained in the molecule, it is not possible to suppress oiliness, stickiness or the like of a cosmetic composition that contains the co-modified organopolysiloxane according to the present invention, and especially a water-in-oil emulsion cosmetic composition, and the feeling to touch of the composition can significantly deteriorate compared to a case in which only the aforementioned sugar alcohol group-containing organic group or the aforementioned glycerin derivative group is contained as a hydrophilic group. In addition, if the average number of repetitions of a glycerin unit is less than the aforementioned lower limit or exceeds the upper limit, the emulsification/dispersion properties of the glycerin derivative-modified silicone deteriorate, it is particularly difficult to emulsify/disperse in an oil phase that contains an organic oil, and it is not possible to obtain a water-in-oil emulsion composition that is stable over a long period of time. Therefore, it is not desirable.

The co-modified organopolysiloxane according to the present invention is represented by the above-mentioned General Formula (1), wherein the $R^1$ groups are each independently a substituted or unsubstituted monovalent hydrocarbon group having 1 to 12 carbon atoms and do not have an oxyalkylene structure having an average number of repetitions of an oxyalkylene unit of 2 or higher. As long as the objective of the present invention is not impaired, $R^1$ in the present invention may be an organic group other than a hydrophilic group. Examples of $R^1$ include a monovalent hydrocarbon group having 1 to 12 carbon atoms that is substituted by an organic group that includes, for example, an alkoxy group, a (meth)acrylic group, an epoxy group, an acyl group, an ester group or a mercapto group, but from the perspective of the emulsification/dispersion properties of the tri-block type co-modified organopolysiloxane, $R^1$ is preferably a halogen atom-substituted or unsubstituted straight chain or branched chain monovalent hydrocarbon group having 1 to 8 carbon atoms, for example an alkyl group such as a methyl group, ethyl group, propyl group, butyl group, pentyl group, hexyl group, heptyl group and octyl group; a cycloalkyl group such as a cyclopentyl group and cyclohexyl group; an alkenyl group such as a vinyl group, allyl group and butenyl group; an aryl group such as a phenyl group and tolyl group; an aralkyl group such as a benzyl group; and a group in which the hydrogen atoms bonded to the carbon atoms in these groups are at least partially substituted with halogen atoms such as fluorine atoms (however, the total number of carbon atoms is 1 to 8). The monovalent hydrocarbon group is preferably a group other than an alkenyl group, and is more preferably a methyl group, an ethyl group, or a phenyl group. It is most preferable for all of the $R^1$ groups to be methyl groups or phenyl groups.

In the above-mentioned General Formula (1), $R^2$ is a substituted or unsubstituted monovalent hydrocarbon group having 13 to 30 carbon atoms, does not have an oxyalkylene structure having an average number of repetitions of an oxyalkylene unit of 2 or higher, and is a characteristic functional group of the tri-block type co-modified organopolysiloxane of the present invention. In the present invention, $R^2$ is a long chain hydrocarbon group having 13 or more carbon atoms, and by having a monovalent hydrocarbon group with such a structure at one molecular chain terminal of a straight chain polysiloxane chain having a specific chain length, compatibility with the organic oil phase on the $R^2$ side in the tri-block type co-modified organopolysiloxane molecule is improved. In this way, a synergetic effect with the specific hydrophilic functional group at the other molecular terminal is achieved, and it is possible to greatly improve the emulsification/dispersion properties of the tri-block type co-modified organopolysiloxane of the present invention not only in, cases where the oil phase is a silicone oil, but particularly in cases where the oil phase is a mixed system of an organic oil and a silicone oil or an oil phase primarily contains an organic oil. From the perspective of emulsification/dispersion properties, $R^2$ is preferably a long chain hydrocarbon group having 14 to 30 carbon atoms, and most preferably a long chain hydrocarbon group having 14 to 24 carbon atoms. Meanwhile, in cases where a monovalent hydrocarbon group in which the number of carbon atoms is less than the aforementioned lower limit is used, it is not possible to sufficiently improve the emulsification/dispersion properties even in the case of a tri-block type co-modified organopolysiloxane having a similar structure and a hydrophilic functional group at a molecular terminal. Moreover, if the number of carbon atoms exceeds the above-mentioned upper limit, the co-modified organopolysiloxane becomes extremely solid (waxy), which is a drawback in terms of feeling to touch in skin care applications in particular, procurement on an industrial scale is difficult, and productivity is poor.

As long as the objective of the present invention is not impaired, $R^2$ may be an organic group other than a hydrophilic group. Examples of $R^2$ include a monovalent hydrocarbon group having 13 to 30 carbon atoms that is substituted by an organic group that includes an alkoxy group, a (meth)acrylic group, an epoxy group, an acyl group, an ester group or a mercapto group, but from the perspective of the emulsification/dispersion properties of the tri-block type co-modified organopolysiloxane, $R^2$ is preferably a halogen atom-substituted or unsubstituted monovalent hydrocarbon group having 14 to 30 carbon atoms, and the structure thereof is selected from among a straight chain, branched and partially branched structure. In the present invention, it is particularly preferable for $R^2$ to be an unsubstituted straight chain monovalent hydrocarbon group. An unsubstituted monovalent hydrocarbon group can be, for example, an alkyl group, aryl group or aralkyl group having 13 to 30 carbon atoms, more preferably 14 to 30 carbon atoms, and most preferably 14 to 24 carbon atoms. Meanwhile, a halogen atoms-substituted monovalent hydrocarbon group can be, for example, a perfluoroalkyl group having 13 to 30 carbon atoms, and more preferably 14 to 30 carbon atoms. This type of monovalent hydrocarbon group is particularly preferably an alkyl group having 14 to 30 carbon atoms, and an example thereof is a group represented by the general formula: —$(CH_2)_v$-$CH_3$ (v is a number in a range of 12 to 29). From the perspective of the emulsification/dispersion properties of the tri-block type co-modified organopolysiloxane, it is most preferable for $R^2$ to be an alkyl group having 14 to 24 carbon atoms.

In the above-mentioned General Formula (1), Q is a sugar alcohol group-containing organic group or a glycerin derivative group having an average number of repetitions of a glycerin unit of 1.1 to 2.9, and is a specific hydrophilic group that does not have an oxyalkylene structure having an average number of repetitions of an oxyalkylene unit of 2 or higher. By having a hydrophilic group, which is the aforementioned sugar alcohol group-containing organic group or the aforementioned glycerin derivative group, at one molecular chain terminal of a straight chain polysiloxane chain having a specific chain length, a synergistic effect with the long chain hydrocarbon group ($R^2$) at the other molecular chain terminal is achieved, and it is possible to greatly improve the emulsification/dispersion properties of the tri-block type co-modified organopolysiloxane of the present invention not only in cases where the oil phase is a silicone oil, but particularly in cases where the oil phase is a mixed system of an organic oil and a silicone oil or an oil phase primarily contains an organic oil.

A detailed explanation of the glycerin derivative group and sugar alcohol group-containing organic group of Q will now be given.

The average number of repetitions of a glycerin unit in the glycerin derivative group of Q is 1.1 to 2.9, preferably 1.5 to 2.4, more preferably 1.8 to 2.2, and most preferably 2. That is, the glycerin derivative group of Q contains mainly a diglycerin derivative group. If the average number of repetitions of a glycerin unit is lower than the aforementioned lower limit or higher than the upper limit, the emulsification/dispersion properties of the tri-block type co-modified organopolysiloxane of the present invention can deteriorate, and it may not be possible to obtain a water-in-oil emulsion composition that is stable over a long period of time.

The number of repetitions of the glycerin unit may be an average value. A content of the diglycerin derivative group in which the number of repetitions of the glycerin unit is 2 is preferably more than 30 wt. %, more preferably 50 wt. % or more, and even more preferably 80 wt. % or more, with respect to all of the other glycerin derivative groups. Most preferable is a pure form in which purity of the diglycerin derivative group is greater than 98 wt. %. That is, the diglycerin derivative-modified silicone of the present invention has an average number of repetitions of a glycerin unit that falls within the above-mentioned range, may be a hydrophilic group that contains mainly a group in which the average number of repetitions is 2, and may be a hydrophilic group that contains only a high purity diglycerin moiety. Meanwhile, a glycerin derivative-modified silicone mixture such as one obtained by blending a refined triglycerin derivative-modified silicone, in which the number of repetitions of a glycerin unit is 3, and a monoglycerin derivative-modified silicone, in which the number of repetitions of a glycerin unit is 1, at an amount of substance ratio of 1:1 cannot be advantageously used in the tri-block type co-modified organopolysiloxane according to the present invention because each component exhibits poor emulsification/dispersion properties.

This type of glycerin derivative group is preferably a diglycerin derivative group-containing organic group which is bonded to a silicon atom via a linking group that is at least divalent and which contains an average of 1.5 to 2.4 of one or more glycerin units selected from among the hydrophilic units represented by Structural Formulae (4-1) to (4-3) below (but which does not contain an oxyalkylene structure having an average number of repetitions of an oxyalkylene unit of 2 or higher in the same functional group). Note that the preferable range of the number of repetitions of each glycerin unit is the same as that described above.

(In this formula, W is a hydrogen atom or an alkyl group having from 1 to 20 carbon atoms)

(In this formula, W is synonymous with the group described above)

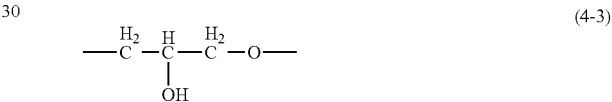

In formulae (4-1) to (4-3), W is a hydrogen atom or an alkyl group having from 1 to 20 carbon atoms, and preferably is a hydrogen atom. Particularly, when W is a hydrogen atom, oxidation in air does not occur easily, and aldehydes such as formaldehyde and the like, and antigenic compounds such as formate esters and the like, are not easily produced over time while in storage. Therefore, when W is a hydrogen atom, there is a benefit of high environmental compatibility.

The diglycerin derivative group has an average number of repetitions of a glycerin unit of 1.5 to 2.4, and more preferably 2, and preferably does not contain a branch in the glycerin unit repeating structure, but it is possible for a part of the structure to be branched, such as a part of the structure being a polyglycerol group or a polyglycidyl ether group.

The divalent linking group is contained in the aforementioned diglycerin derivative group, is a bonding site to a silicon atom, and is a divalent organic group that does not contain an oxyalkylene structure having an average number of repetitions of an oxyalkylene unit of 2 or higher. Specifically, the divalent linking group is a straight chain or branched chain alkylene group such as an ethylene group, propylene group, butylene group and hexylene group; an alkylene phenylene group such as an ethylene phenylene group and propylene phenylene group; an alkylene aralkylene group such as an ethylene benzylene group; an alkylenoxyphenylene group such as an ethylenoxyphenylene group and propylenoxyphenylene group; or an alkylenoxybenzylene group such as a methylenoxybenzylene group, ethylenoxybenzylene group and propylenoxybenzylene group. The divalent linking group is most preferably selected from among the divalent organic groups represented by the general formulae below.

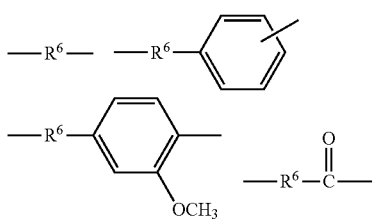

(In these formulae, $R^6$ may have a substituent, and are each independently a straight or branched chain alkylene group or alkenylene group having from 2 to 22 carbon atoms, or an arylene group having from 6 to 22 carbon atoms)

The diglycerin derivative group is more preferably a diglycerin derivative group represented by structural formula (5) below:

  (5)

In the formula, $R^5$ is a divalent organic group that does not contain an oxyalkylene structure having an average number of repetitions of an oxyalkylene unit of 2 or higher, and examples thereof include groups similar to the above-mentioned divalent linking groups. X is at least one type of glycerin unit selected from the hydrophilic units represented by the Structural Formulae (4-1) to (4-3). m represents the number of repetitions of the glycerin unit, and is on average, a number in a range from 1.5 to 2.4. Note that the preferable range of the number of repetitions of each glycerin unit is the same as that described above.

It is most preferable for the diglycerin derivative group-containing organic group to be a diglycerin derivative group-containing organic group represented by General Formula (5-1) below:

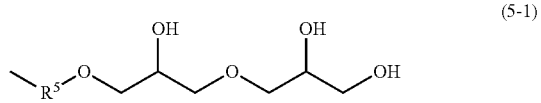 (5-1)

(In the formula, $R^5$ is a divalent organic group that does not contain an oxyalkylene structure having an average number of repetitions of an oxyalkylene unit of 2 or higher) or General Formula (5-2) below:

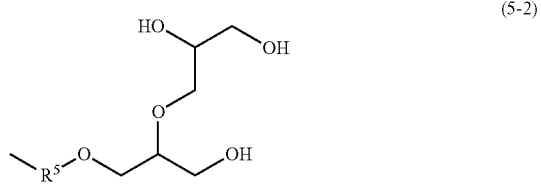 (5-2)

(wherein $R^5$ is synonymous with that described above).

In the tri-block type co-modified organopolysiloxane according to the present invention, the diglycerin derivative group-containing organic group is preferably a hydrophilic groups derived from a diglycerin monoallyl ether or a diglyceryl eugenol.

In General Formula (1), the structure of the sugar alcohol group-containing organic group of Q is not limited as long as the group does not contain an oxyalkylene structure having an average number of repetitions of an oxyalkylene unit of 2 or higher and has a sugar alcohol moiety, but it is preferable for a sugar alcohol residue to be bonded to a silicon atom via a divalent organic group (excluding a group having an oxyalkylene structure having an average number of repetitions of an oxyalkylene unit of 2 or higher).

Therefore, Q is preferably a sugar alcohol group-containing organic group represented by Structural Formulae (3-1) to (3-2) below:

Structural Formulae (3-1) to (3-2):

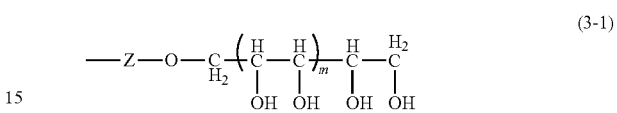 (3-1)

(In the formula, Z is a divalent organic group (excluding a group having an oxyalkylene structure having an average number of repetitions of an oxyalkylene unit of 2 or higher), and m is 1 or 2)

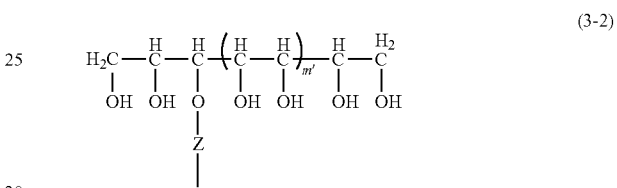 (3-2)

(In the formula, Z is synonymous with that described above, and m' is 0 or 1)

The aforementioned sugar alcohol-modified silicone is characterized by at least one of the sugar alcohol group-containing organic groups represented by Structural Formulae (3-1) to (3-2) above being bonded to a silicon atom. The divalent organic group of Z in General Formula (3-1) or (3-2) is a divalent organic group that does not contain an oxyalkylene structure having an average number of repetitions of an oxyalkylene unit of 2 or higher, and examples thereof include groups similar to the above-mentioned divalent linking groups.

The sugar alcohol group-containing organic group of Q is particularly preferably a sugar alcohol group-containing organic group in which Z is a propylene group and m=1 in General Formula (3-1). Similarly, the sugar alcohol group-containing organic group of Q is particularly preferably a sugar alcohol group-containing organic group in which Z is a propylene group and m'=0 in General Formula (3-2). In such cases, the sugar alcohol group-containing organic group is a xylitol residue represented by the structural formula: $-C_3H_6-OCH_2[CH(OH)]_3CH_2OH$ or the structural formula: $-C_3H_6-OCH\{CH(OH)CH_2OH\}_2$, which correspond to structural formula (3-1) or (3-2) respectively (hereinafter referred to simply as "xylitol residue" or "xylitol-modified group").

As mentioned above, the xylitol residue is a group represented by the structural formula: $-C_3H_6-OCH_2[CH(OH)]_3CH_2OH$ or the structural formula: $-C_3H_6-OCH\{CH(OH)CH_2OH\}_2$, but it is possible to use one or two of these xylitol residues in the tri-block type co-modified organopolysiloxane according to the present invention. Therefore, it is possible for all of the Q groups in the above-mentioned General Formula (1) to comprise only a xylitol residue represented by the structural formula:

—C₃H₆—OCH₂[CH(OH)]₃CH₂OH or the structural formula: —C₃H₆—OCH{CH(OH)CH₂OH}₂ or for Q to be constituted from the two types of xylitol residue represented by the structural formula: —C₃H₆—OCH₂[CH(OH)]₃CH₂OH and the structural formula: —C₃H₆—OCH{CH(OH)CH₂OH}₂. In the latter case, the compositional ratio (amount of substance ratio) is preferably between 5:5 and 10:0, and more preferably between 8:2 and 10:0. Moreover, if this compositional ratio is 10:0, Q essentially comprises only a xylitol residue represented by the structural formula: —C₃H₆—OCH₂[CH(OH)]₃CH₂OH.

In addition, in cases where the tri-block type co-modified organopolysiloxane according to the present invention is a mixture of two or more types of sugar alcohol-modified organopolysiloxane, this mixture can contain a tri-block type co-modified organopolysiloxane in which Q in the above-mentioned General Formula (1) comprises only a xylitol residue represented by the structural formula: —C₃H₆—OCH₂[CH(OH)]₃CH₂OH, a tri-block type co-modified organopolysiloxane in which Q in the above-mentioned General Formula (1) comprises only a xylitol residue represented by the structural formula: —C₃H₆—OCH{CH(OH)CH₂OH}₂, or two types of tri-block type co-modified organopolysiloxane selected from among the group comprising sugar alcohol-modified organopolysiloxanes in which Q in the above-mentioned General Formula (1) is constituted from two types of xylitol residue represented by the structural formula: —C₃H₆—OCH₂[CH(OH)]₃CH₂OH and the structural formula: —C₃H₆—OCH{CH(OH)CH₂OH}₂ (the compositional ratio (amount of substance ratio) is preferably between 5:5 and 10:0, and more preferably between 8:2 and 10:0). Furthermore, the tri-block type co-modified organopolysiloxane according to the present invention may be a mixture of at least two types of tri-block type co-modified organopolysiloxane having different compositional ratios, in which Q in General Formula (1) is constituted from two types of xylitol residue represented by the structural formula: —C₃H₆—OCH₂[CH(OH)]₃CH₂OH and the structural formula: —C₃H₆—OCH{CH(OH)CH₂OH}₂ (the compositional ratio (amount of substance ratio) is preferably between 5:5 and 10:0, and more preferably between 8:2 and 10:0).

The tri-block type co-modified organopolysiloxane according to the present invention is modified by a hydrophilic group that is a diglycerin derivative group or sugar alcohol group-containing organic group, and is characterized in that the other molecular chain terminal is modified by a monovalent hydrocarbon group having 13 to 30 carbon atoms and the degree of polymerization of the straight chain polysiloxane chain falls within a specific range.

Specifically, n is a number in a range of 0 to 100 in General Formula (1), and when n is 0, the tri-block type co-modified organopolysiloxane according to the present invention is a both terminal co-modified disiloxane. From the perspective of emulsification or dispersion performance when used as an emulsifier for a water-in-oil emulsion or a powder-in-oil dispersing agent, n is preferably in a range of 0 to 80, and more preferably in a range of 0 to 60.

(Tri-Block Type Co-Modified Organopolysiloxane Synthesis Reaction)
The aforementioned tri-block type co-modified organopolysiloxane can be obtained by means of an addition reaction of a hydrocarbon having 13 to 30 carbon atoms and having one reactive unsaturated group at one molecular chain terminal per molecule and a diglycerin derivative having a reactive functional group at one molecular chain terminal or a sugar alcohol-containing organic compound to a straight chain organopolysiloxane having a specific chain length and having a reactive functional group at both molecular terminals. The type of addition reaction is not particularly limited but, from the standpoint of reaction control, purity, and yield, the addition reaction is preferably performed in the presence of a hydrosilylation reaction catalyst.

More specifically, an example thereof is a production method in which (A) an organopolysiloxane represented by General Formula (1') below, which has a silicon-bonded hydrogen atom at both molecular terminals, and (B) a hydrocarbon compound having 13 to 30 carbon atoms and having one reactive unsaturated group at one molecular chain terminal per molecule (at a quantity corresponding to approximately half the molar equivalent of component (A)) are subjected to addition reaction in the presence of (C) a hydrosilylation reaction catalyst, and then (D) a diglycerin derivative having one alkenyl group at a molecular chain terminal or a sugar alcohol-containing organic compound is further addition reacted (at a quantity corresponding to approximately half the molar equivalent of component (A)) to the product of the aforementioned addition reaction.

General Formula (1'):

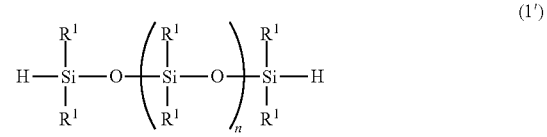

(1')

(In the formula, R¹ is synonymous with the groups described and n is a number that falls within a range similar to that mentioned above)

The hydrocarbon compound having one reactive unsaturated group per molecule (B), which is used in the synthesis of the aforementioned tri-block type co-modified organopolysiloxane, is preferably a monounsaturated hydrocarbon having 13 to 30 carbon atoms, and more preferably a 1-alkene. Examples of the 1-alkene include 1-tridecene, 1-tetradecene, 1-hexadecene, 1-octadecene and the like.

A diglycerin derivative having one reactive unsaturated group per molecule (C-1), which is used in the synthesis of the aforementioned tri-block type co-modified organopolysiloxane, is preferably a diglycerin derivative having a carbon-carbon double bond at a molecular chain terminal. These are diglycerin derivatives having a reactive functional group, such as an alkenyl group, at a molecular chain terminal, such as allyl diglycerol, allyl diglycidyl ether, diglycerin monoallyl ether and diglyceryl eugenol, and can be synthesized using a publicly known method.

With the tri-block type co-modified organopolysiloxane according to the present invention, from the perspectives of use as a surfactant or dispersing agent that can produce a stable composition having an oil agent as the continuous phase (a water-in-oil emulsion composition or a powder-in-oil dispersion), such as an emulsifier for a water-in-oil emulsion, and from the perspectives of use in a cosmetic compositions, component (a) is specifically diglycerin monoallyl ether or diglyceryl eugenol.

Similarly, a sugar alcohol functional organic compound having one reactive unsaturated group per molecule (C-2), which is used in the synthesis of the tri-block type co-modified organopolysiloxane, is preferably a monounsaturated ether compound of a sugar alcohol represented by General Formula (4'-1) below:

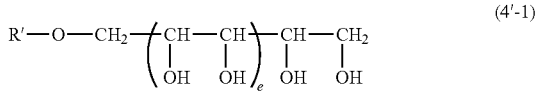

(4'-1)

(In the formula, R' is an unsaturated organic group, and e is 1 or 2, and preferably 1), or General Formula (4'-2) below:

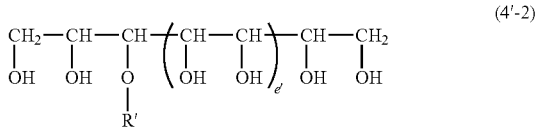

(4'-2)

(In the formula, R' is an unsaturated organic group, and e' is 0 or 1, and preferably 0).

The unsaturated organic group is not particularly limited as long as the group comprises an unsaturated group, but is preferably a substituted or unsubstituted, straight or branched unsaturated hydrocarbon group having 3 to 5 carbon atoms. Examples of the unsaturated hydrocarbon group having from 3 to 5 carbon atoms include allyl groups, butenyl groups, methallyl groups, and similar alkenyl groups; and allyl groups are preferable.

The aforementioned monounsaturated ether compound of a sugar alcohol is preferably a monoallyl ether of a sugar alcohol, and more preferably a xylitol monoallyl ether represented by the structural formula: $CH_2=CH-CH_2-OCH_2[CH(OH)]_3CH_2OH$ or the structural formula: $CH_2=CH-CH_2-OCH\{CH(OH)CH_2OH\}_2$ (hereinafter referred to as a "xylitol monoallyl ether"). The xylitol monoallyl ether can be synthesized using a publicly known method.

The xylitol monoallyl ether may be a compound represented by either the structural formula: $CH_2=CH-CH_2-OCH_2[CH(OH)]_3CH_2OH$ or the structural formula: $CH_2=CH-CH_2-OCH\{CH(OH)CH_2OH\}_2$, or a mixture thereof, and is not particularly limited. In particular, it is preferable for the xylitol monoallyl ether represented by the structural formula: $CH_2=CH-CH_2-OCH_2[CH(OH)]_3CH_2OH$ or the structural formula: $CH_2=CH-CH_2-OCH\{CH(OH)CH_2OH\}_2$ to be refined and used as a raw material, or for a xylitol monoallyl ether that contains the xylitol monoallyl ether represented by the structural formula: $CH_2=CH-CH_2-OCH_2[CH(OH)]_3CH_2OH$ and the xylitol monoallyl ether represented by the structural formula: $CH_2=CH-CH_2-OCH\{CH(OH)CH_2OH\}_2$ at an amount of substance ratio of between 5:5 and 10:0 to be used as a raw material, and, in the latter case, more preferable to use xylitol monoallyl ether in which the compositional ratio is between 8:2 and 10:0. Moreover, if the compositional ratio is 10:0, the raw material is essentially a refined product comprising only a xylitol monoallyl ether represented by the structural formula: $CH_2=CH-CH_2-OCH_2[CH(OH)]_3CH_2OH$.

The hydrosilylation reaction used to synthesize the tri-block type co-modified organopolysiloxane can be carried out using a publicly known method in the presence or absence of a solvent. Here, the reaction solvent can be an alcoholic solvent such as ethanol and isopropyl alcohol, an aromatic hydrocarbon-based solvent such as toluene and xylene; an ether-based solvent such as dioxane and THF; an aliphatic hydrocarbon-based solvent such as n-hexane, cyclohexane, n-heptane, cycloheptane and methylcyclohexane; or a chlorinated hydrocarbon-based organic solvent such as carbon tetrachloride.

The hydrosilylation reaction may be performed in the presence or absence of a catalyst, but preferably is performed in the presence of a catalyst because the reaction can be carried out at a low temperature and in a shorter period of time. Examples of the catalyst include platinum, ruthenium, rhodium, palladium, osmium, iridium, and similar compounds, and platinum compounds are particularly effective due to their high catalytic activity. Examples of the platinum compound include chloroplatinic acid; platinum metal; platinum metal supported on a carrier such as platinum supported on alumina, platinum supported on silica, platinum supported on carbon black, and the like; and a platinum complex such as platinum-vinylsiloxane complex, platinum phosphine complex, platinum-phosphite complex, platinum alcoholate catalyst, and the like. If a platinum catalyst is used, the usage quantity of the solvent is approximately 0.0001 to 0.1 wt. %, and preferably 0.0005 to 0.05 wt. %, relative to the weight of the metal catalyst, but is not particularly limited.

A reaction temperature of the hydrosilylation reaction is typically from 30 to 120° C., and a reaction time is typically from 10 minutes to 24 hours and preferably from 1 to 10 hours.

In addition, when synthesizing the tri-block type co-modified organopolysiloxane according to the present application, it is possible to use the method for reacting, refining and deodorizing with an acidic substance disclosed by the applicants in paragraphs [0110] to [0122] of Patent Document 31 (WO 2011/049248). In particular, the tri-block type co-modified organopolysiloxane of the present invention is mainly used as a cosmetic compositions or external use preparation, and from the perspectives of safety and odor, is most preferably subjected to refining and deodorization with an acidic substance.

From the perspective of deodorization, the tri-block type co-modified organopolysiloxane of the present invention is preferably treated with one or more types of acidic inorganic salt (preferably sodium hydrogen sulfate and the like) which is solid at 25° C., which is water-soluble and in which an aqueous solution obtained by dissolving 50 g of the acidic inorganic salt in 1 L of ion exchanged water has a pH of 4 or lower at 25° C. For example, this means (1) carrying out decomposition treatment by adding the above-mentioned acidic inorganic salt to a reaction system of a diglycerin derivative-modified polysiloxane composition synthesized using a hydrosilylation reaction, and then stirring and (2) carrying out hydrolysis treatment by adding an acidic inorganic salt and water or an acidic inorganic salt, water and a hydrophilic solvent and then stirring. The treatment process that uses the acidic inorganic salt is preferably carried out in the presence of water and/or a hydrophilic solvent.

After carrying out the above-mentioned deodorization treatment, it is preferable to include a stripping step in which low boiling point components (propionaldehyde and the like), which are odor-causing substances, are removed, and it is preferable to carry out the above-mentioned treatment using an acidic substance and stripping of odor-causing substances a plurality of times.

In addition, after the aforementioned acidizing process, adding an amount corresponding to 100 ppm to 50,000 ppm of an alkaline buffer (sodium phosphate, potassium phosphate, sodium citrate, sodium acetate, or the like) into the obtained tri-block type co-modified organopolysiloxane or a composition thereof is preferable from the perspective of reducing odor.

(Use of the Tri-Block Type Co-Modified Organopolysiloxane)

The tri-block type co-modified organopolysiloxane of the present invention exhibits particularly excellent emulsification performance when used alone, and can therefore finely and stably emulsify/disperse an aqueous phase, powder or the like not only in cases where the oil phase is a silicone oil, ester oil or triglyceride, but also in cases where the oil phase is primarily a non-polar organic oil such as a mineral oil and isododecane, which was difficult with conventional glycerin-modified silicones or sugar-modified silicones, and can therefore produce a composition having excellent stability over time or when subjected to heat. In particular, the tri-block type co-modified organopolysiloxane of the present invention has a hydrophobic long chain alkyl group, a silicone backbone and a specific hydrophilic group in a regular arrangement in the molecule, and because the balance between these is excellent. Therefore, the tri-block type co-modified organopolysiloxane of the present invention is extremely useful as a surfactant or dispersing agent that can produce a stable composition having an oil agent as the continuous phase in a wide variety of oil agent systems (a water-in-oil emulsion composition, a polyol-in-oil type emulsion composition, a polar solvent-in-oil type emulsion composition or a powder-in-oil dispersion). The tri-block type co-modified organopolysiloxane of the present invention is particularly suitable as an emulsifier for a water-in-oil emulsion or a powder-in-oil dispersing agent.

In addition, the tri-block type co-modified organopolysiloxane of the present invention can stabilize a wide variety of oil agent-containing emulsion systems in a variety of oil agent-containing W/O emulsion formulations without being aided by an oil gelling agent such as an organic emulsifier, a polyether-modified silicone and a clay mineral that has been hydrophobized/oil-swelled by means of a quaternary ammonium salt-based organic cation, and can therefore maximize the synergistic effect in terms of feeling to touch of an oil agent and said tri-block type co-modified organopolysiloxane and provide a W/O emulsion type external use preparation or cosmetic composition having a soft and natural feeling to touch, light smoothness, good spreadability and excellent moisture retention.

In addition, use of the novel tri-block type co-modified organopolysiloxane according to the present invention as a surfactant is the same as the use of the co-modified organopolysiloxane disclosed by the applicants in paragraphs [0124] to [0147] of the above-mentioned Patent Document 31 (WO 2011/049248) as a surfactant and the preparation of a variety of emulsion composition, and the tri-block type co-modified organopolysiloxane according to the present invention is particularly suitable as a surfactant used in a water-in-oil emulsion cosmetic composition.

<Surfactant, Dispersing Agent and Emulsifier for Water-in-Oil Emulsion>

The tri-block type co-modified organopolysiloxane of the present invention can be used as a surfactant or a dispersing agent that can produce a stable composition having an oil agent as the continuous phase (a water-in-oil emulsion composition, a polyol-in-oil type emulsion composition, a polar solvent-in-oil type emulsion composition or a powder-in-oil dispersion). In particular, the emulsifier for a water-in-oil emulsion can be advantageously used not only as an emulsifier for an ordinary water-in-oil emulsion in which an aqueous phase is dispersed in an oil phase, but also as an emulsifier for a polyol-in-oil type emulsion in which a polyol phase is dispersed in an oil phase or as an emulsifier for a polar solvent-in-oil type emulsion in which a polar solvent is dispersed in a non-polar oil phase. Furthermore, the tri-block type co-modified organopolysiloxane of the present invention exhibits excellent performance as a dispersing agent that uniformly disperses a variety of powders in an oil phase, and can therefore also be used as a powder dispersing agent when preparing a water-in-oil emulsion.

A surfactant, dispersing agent and emulsifier for a water-in-oil emulsion that contains the tri-block type co-modified organopolysiloxane of the present invention is suitable for use in a cosmetic composition or external use preparation, and can be preferably blended as a raw material for a variety of cosmetic compositions and external use preparations. In particular, it is preferable to use said tri-block type co-modified organopolysiloxane at a quantity of approximately 0.1 to 40 wt. % relative to the total weight of a cosmetic composition or external use preparation.

Unlike a conventional polyether-modified silicone, the tri-block type co-modified organopolysiloxane of the present invention is hardly susceptible to deterioration due to oxidation by oxygen in the air. Thus, it is not necessary to add a phenol, a hydroquinone, a benzoquinone, an aromatic amine, a vitamin, or similar antioxidant in order to prevent oxidation deterioration; or take steps to increase oxidation stability. However, adding such an antioxidant, for example, BHT(2,6-di-t-butyl-p-cresol), vitamin E, or the like, will result in a further increase in stability. In this case, an added amount of the antioxidant that is used is in a range (by weight (mass)) from 10 to 1,000 ppm, and preferably from 50 to 500 ppm, of the tri-block type co-modified organopolysiloxane.

(Other Uses)

The triblock co-modified organopolysiloxane according to the present invention can also be used as a tactile sensation improver, a moisturizing agent, a binder, a surface treatment agent, and a skin adhesive. Additionally, the triblock co-modified organopolysiloxane according to the present invention can be combined with water for use as a film agent or a viscosity adjusting agent.

(Raw Material for Use in an External Use Preparation or a Cosmetic Composition)

A proportion of the tri-block type co-modified organopolysiloxane in the raw material for an external use preparation and a cosmetic composition is preferably from 10 to 100 wt. % (mass %), more preferably from 20 to 100 wt. % (mass %), and even more preferably from 30 to 100 wt. % (mass %) based on the total weight (mass) of the raw material. This is because the tri-block type co-modified organopolysiloxane according to the present invention can be used as a raw material of an external use preparation or cosmetic composition by being diluted in a suitable solvent, such as a silicone oil, an organic oil and an alcohol. A proportion of the raw material compounded in the external use preparation or the cosmetic composition is not particularly limited but, for example, can be from 0.1 to 40 wt. % (mass %), and is preferably from 1 to 30 wt. % (mass %), more preferably from 2 to 20 wt. % (mass %), and even more preferably from 3 to 10 wt. % (mass %) based on the total weight (mass) of the external use preparation or the cosmetic composition.

(External Use Preparation and Cosmetic Composition)

The tri-block type co-modified organopolysiloxane of the present invention can be blended preferably in an external use preparation or a cosmetic composition and can constitute the external use preparation or cosmetic composition of the present invention. In particular, the tri-block type co-modified organopolysiloxane of the present invention exhibits particularly excellent emulsification performance when used alone, and can finely and stably emulsify/disperse an aqueous phase, powder or the like not only in cases where the oil phase is a silicone oil, ester oil or triglyceride, but also in cases where the oil phase is a non-polar organic oil such as a mineral oil and isododecane, which was difficult with conventional glycerin-modified silicones or sugar-modified silicones. As a result, the tri-block type co-modified organopolysiloxane of the present invention can provide a composition having excellent stability over time or when subjected to heat, and can be preferably blended in an external use preparation or cosmetic composition that is in the form of a water-in-oil emulsion.

In addition, the tri-block type co-modified organopolysiloxane of the present invention exhibits far better emulsification performance when used alone than a conventional glycerin-modified silicone or sugar-modified silicone, and therefore has the advantage of being able to design a stable formulation or preparation of a cosmetic product without blending a compound having an oxyalkylene structure having an average number of repetitions of an oxyalkylene unit of 2 or higher, and specifically a non-ionic surfactant having a polyoxyalkylene structure. Furthermore, the diglycerin derivative-containing group and sugar alcohol group-containing organic group do not suffer from the problem of oxidative deterioration due to not having a polyoxyethylene (PEG) structure and, unlike a non-ionic surfactant having a polyoxyalkylene structure (for example, a polyether-modified silicone), suppress oiliness or stickiness in an external use preparation or cosmetic composition that is in the form of a water-in-oil emulsion and can produce a W/O emulsion type external use preparation or cosmetic composition having a soft and natural feeling to touch, light smoothness, good spreadability and excellent moisture retention.

Therefore, the problem of oxidative deterioration of polyoxyethylene (PEG) is substantially ameliorated in an external use preparation or cosmetic composition that contains the tri-block type co-modified organopolysiloxane of the present invention, and it is highly preferable not to blend a compound having an oxyalkylene structure having an average number of repetitions of an oxyalkylene unit of 2 or higher when selecting a completely PEG-FREE formulation as the constitution of an end consumer product having an excellent feeling to touch, such as a cosmetic product. In addition, it is difficult to achieve this objective when using a conventional glycerin-modified silicone or sugar-modified silicone rather than the tri-block type co-modified organopolysiloxane of the present invention.

The external use preparation is a product to be applied to human skin, nails, hair, and the like and, for example, medicament active ingredients can be compounded therein and used in the treatment of various disorders. The cosmetic composition is also a product to be applied to human skin, nails, hair, and the like, and is used for beauty purposes. The external use preparation or cosmetic composition is not limited, but is preferably an anti-perspirant, a skin cleansing agent, a skin conditioner, a skin cosmetic composition product, a make-up composition product, an oil-based cosmetic composition product, a skin care cosmetic composition product, a hair cleansing agent, an external use preparation for hair or a hair cosmetic composition product.

The anti-perspirant, skin cleansing agent, skin conditioner or skin cosmetic composition product according to the present invention contains an emulsifier for a water-in-oil emulsion or powder dispersing agent that contains the tri-block type co-modified organopolysiloxane of the present invention, and the form thereof is not particularly limited, but may be in the form of a solution, milk-like, cream-like, solid, semi-solid, paste-like, gel-like, powder-like, multi-layer, mousse-like, or a water-in-oil or oil-in-water emulsion composition. Specific examples of the skin external use preparation or the skin cosmetic composition product according to the present invention include toilet water, emulsions, creams, sunscreen emulsions, sunscreen creams, hand creams, cleansing compositions, massage lotions, cleansing agents, anti-perspirants, deodorants, and similar basic cosmetic products; foundations, make-up bases, blushers, rouges, eye shadows, eye liners, mascaras, nail enamels, and similar make-up cosmetic products; and the like.

Similarly, the hair cleansing agent, the hair external use preparation or the hair cosmetic composition product according to the present invention contains the tri-block type co-modified organopolysiloxane of the present invention and can be used in various forms. For example, the hair cleansing agent, the hair external use preparation or the hair cosmetic composition product according to the present invention may be dissolved or dispersed in an alcohol, a hydrocarbon, a volatile cyclic silicone, or the like and used; furthermore, these may be used in the form of an emulsion by dispersing a desired emulsifier in water. Additionally, the hair cleansing agent, the hair external use preparation or the hair cosmetic composition product according to the present invention can be used as a spray by using propane, butane, trichloromonofluoromethane, dichlorodifluoromethane, dichlorotetrafluoroethane, carbonic acid gas, nitrogen gas, or a similar propellant. Examples of other forms include milk-like, cream-like, solid, semi-solid, paste-like, gel-like, powder-like, multi-layer, mousse-like, and similar forms. There various forms can be used as shampooing agents, rinsing agents, conditioning agents, setting lotions, hair sprays, permanent wave agents, mousses, hair colorants, and the like.

The type, form and container of other cosmetic composition or preparation for external use according to the present invention are the same as those disclosed by the applicants in paragraphs [0230] to [0233] and so on of the above-mentioned Patent Document 31 (WO 2011/049248).

The following other components generally used in external use preparations or cosmetic compositions may be added to the external use preparation or the cosmetic composition of the present invention, provided that such components do not inhibit the effectiveness of the present invention: water, powders or coloring agents, alcohols, water-soluble polymers, film-forming agents, oil agents, oil-soluble gelling agents, organo-modified clay minerals, surfactants, resins, UV absorbers, salts, moisturizing agents, preservatives, antimicrobial agents, perfumes, salts, antioxidants, pH adjusting agents, chelating agents, refreshing agents, anti-inflammatory agents, skin beautifying components (skin-lightening agents, cell activating agents, agents for ameliorating skin roughness, circulation promoters, astringents, antiseborrheic agents, and the like), vitamins, amino acids, nucleic acids, hormones, clathrates, and the like; bioactive substances, medicament active ingredients, and perfumes. However, the additives are not particularly limited to thereto.

(E) Powder or Coloring Agent

A powder or coloring agent (E), which is used in the cosmetic composition or external use preparation according to the present invention, is one that is commonly used as a component of a cosmetic composition, and includes white or colored pigments and extender pigments. The white and colored pigments are used to impart color and the like to the cosmetic composition, and the extender pigments are used to improve the feeling to touch and the like of the cosmetic composition. In the present invention, white and colored pigments as well as extender pigments commonly used in cosmetic compositions can be used as the powder without any particular restriction. In the present invention, preferably, one or two or more of the powders are compounded. The form (sphere, bar, needle, plate, amorphous, spindle, cocoon, or the like), particle size (aerosol, micro-particle, pigment-grade particle, or the like), and particle structure (porous, nonporous, or the like) of the powder are not limited in any way, but an average primary particle size is preferably in a range from 1 nm to 100 µm. When compounding the powder and/or coloring agent as a pigment, preferably one or two or more selected from an inorganic pigment powder, an organic pigment powder, and a resin powder having an average diameter in a range from 1 nm to 20 µm is compounded.

Examples of the powder include inorganic powders, organic powders, surfactant metal salt powders (metallic soaps), colored pigments, pearl pigments, metal powder pigments, and the like. In addition, compound products of the powders can also be used. Furthermore, it is possible to subject the surface of these to water-repellent treatment.

These specific examples are the same as the powders and coloring agents disclosed by the applicants in paragraphs [0150] to [0152] of the above-mentioned Patent Document 31 (WO 2011/049248).

In addition, by subjecting these powders or coloring agents to surface treatment with an emulsifier for a water-in-oil emulsion or powder dispersing agent that contains the aforementioned tri-block type copolymer, it is possible to achieve a smooth, soft and moist feeling to touch. Furthermore, when blending a water-in-oil emulsion or powder dispersing agent that contains the aforementioned tri-block type copolymer in addition to these powders or coloring agents in a cosmetic composition, it is possible to improve the dispersion stability of said powder in the overall cosmetic composition and obtain a cosmetic composition that is stable over time.

Of the exemplified powders, a particular explanation will be given of a silicone elastomer powder. The silicone elastomer powder is a crosslinked product of a straight diorganopolysiloxane formed principally from diorganosiloxy units (D units), and can be preferably obtained by crosslinking an organohydrogenpolysiloxane having a silicon-bonded hydrogen atom on the side chain or the molecular terminal and a diorganopolysiloxane having an unsaturated hydrocarbon group such as an alkenyl group and the like on the side chain or the molecular terminal, in the presence of a hydrosilylation reaction catalyst. Compared to a silicone resin powder formed from T units and Q units, the silicone elastomer powder is soft, has elasticity, and has superior oil absorbency. Therefore, oils and fats on the skin can be absorbed and makeup smearing can be prevented. In addition, by carrying out surface treatment using an emulsifier for a water-in-oil emulsion or powder dispersing agent that contains the aforementioned tri-block type co-modified organopolysiloxane, it is possible to impart a moist feeling to touch without reducing the suede-like feeling to touch of a silicone elastomer powder. Furthermore, when blending an emulsifier for a water-in-oil emulsion that contains the aforementioned tri-block type co-modified organopolysiloxane in addition to a silicone elastomer powder in a cosmetic composition, it is possible to improve the dispersion stability of said powder in the overall cosmetic composition and obtain a cosmetic composition that is stable over time.

The silicone elastomer powder can be in various forms such as spherical, flat, amorphous, and the like. The silicone elastomer powder may be in the form of an oil dispersion. With the cosmetic composition of the present invention, a silicone elastomer powder having a particle shape, having a primary particle size in a range of 0.1 to 50 µm observed using an electron microscope and/or the average primary particle size in a range of 0.1 to 50 µm measured by laser diffraction/scattering method, and having spherical primary particles can be preferably compounded. The silicone elastomer that constitutes the silicone elastomer powder is preferably one having a hardness, as measured using a type A durometer in the "Rubber, Vulcanized or Thermoplastic—Determination of Hardness" specified in JIS K 6253, of 80 or lower, and more preferably 65 or lower.

Of these silicone elastomer powders, specific examples of silicone elastomer spherical powders are the same as those disclosed by the applicants in paragraph [0168] of the above-mentioned Patent Document 31 (WO 2011/049248), and may be a silicone elastomer powder that has been subjected to a variety of water-repellent treatments, as disclosed in paragraphs [0150] to [0152].

(U) Oil Agent

The oil agent used in the cosmetic composition or external use preparation according to the present invention is preferably one or more oil agents selected from among silicone oils, non-polar organic compounds and lowly polar to highly polar organic compounds that are liquid at 5 to 100° C. (U), and the non-polar organic compound and lowly polar to highly polar organic compound are preferably a hydrocarbon oil, fatty acid ester oil or liquid fatty acid triglyceride. These oil agents are particularly widely used as base materials for cosmetic compositions, and it is possible to additionally use one or more types of compounds selected from among publicly known vegetable oils and fats, animal oils and fats, higher alcohols, liquid fatty acid triglycerides, artificial sebum and fluorine-based oils. Because an emulsifier for a water-in-oil emulsion or powder dispersing agent that contains the aforementioned tri-block type co-modified organopolysiloxane exhibits excellent compatibility with, and dispersibility in, these non-silicone-based oil agents, it is possible to stably blend a hydrocarbon oil or fatty acid ester oil in a cosmetic composition and also possible to utilize the moisture retention characteristics of these non-silicone-based oil agents. Therefore, an emulsifier for a water-in-oil emulsion or powder dispersing agent that contains the aforementioned tri-block type co-modified organopolysiloxane can improve the compounding stability in a cosmetic composition of these non-silicone-based oil agents.

In addition, by using a hydrocarbon oil and/or fatty acid ester oil in combination with a silicone oil, it is possible to retain moisture in the skin in addition to the refreshing feeling to touch inherent in silicone oils and impart a cosmetic composition with a moisturizing feel (also known as a "luxurious feeling to touch") that moisturizes skin and hair and a smooth feeling to touch, and this also has the advantage of not impairing the stability over time of a cosmetic composition. Furthermore, with a cosmetic composition comprising the hydrocarbon oil and/or fatty acid ester oil and the silicone oil, these moisturizing components (the hydrocarbon oil and/or the fatty acid ester oil) can be applied on the skin or hair in a more stable and uniform manner. Therefore, the moisturizing effects of the moisturizing components on the skin are improved. Thus, compared to a cosmetic composition comprising only a non-silicone-based oil agent (e.g. a hydrocarbon oil, a fatty acid ester oil, or the like), the cosmetic composition comprising a nonsilicone-based oil agent along with a silicone oil is advantageous in that a smoother, more luxurious feeling to touch is imparted.

These oil agents are the same as those disclosed by the applicants in paragraphs [0130] to [0135] and [0206] and so on in the above-mentioned Patent Document 31 (WO 2011/049248). Examples of the fluorine-based oil include perfluoropolyether, perfluorodecalin, perfluorooctane, and the like.

It is possible to further blend water (T) in the cosmetic composition or external use preparation of the present invention, and the cosmetic composition or external use preparation of the present invention may be in the form of a water-in-oil emulsion. In this case, the cosmetic composition of the present invention or the external use preparation displays superior emulsion stability and sensation during use. The preparation of a hydrous cosmetic composition and emulsion cosmetic composition is the same as that disclosed by the applicants in paragraphs [0128] to [0146] in the above-mentioned Patent Document 31 (WO 2011/049248).

It is possible to further blend another surfactant (F) in the cosmetic composition or external use preparation of the present invention. These surfactants are cleansing components for skin or hair or components that function as emulsifiers for oil agents, and can be selected as appropriate according to the type and function of the cosmetic composition. More specifically, other surfactants can be selected from among the group comprising anionic surfactants, cationic surfactants, non-ionic surfactants, amphoteric surfactants and semipolar surfactants, but use in combination with a silicone-based non-ionic surfactant is particularly preferred.

These surfactants are the same as those disclosed by the applicants in paragraphs [0162], [0163] and [0195] to [0201] and so on in the above-mentioned Patent Document 31 (WO 2011/049248). The emulsifier for a water-in-oil emulsion that contains the aforementioned tri-block type co-modified organopolysiloxane used in the present invention has a hydrophilic moiety and a hydrophobic moiety in the molecule, and therefore functions as a powder-in-oil dispersing agent. Therefore, when combined with a silicone-based non-ionic surfactant, the liquid organopolysiloxane functions as an aid to enhance the stability of the non-ionic surfactant, and may improve the overall stability of the formulation. In particular, the aforementioned tri-block type co-modified organopolysiloxane can be advantageously used in combination with a polyglycerin-modified silicone, a glycerin-modified silicone, a sugar-modified silicone and a sugar alcohol-modified silicone. Moreover, as necessary, a silicone-based nonionic surfactant in which an alkyl branch, a straight chain silicone branch, a siloxane dendrimer branch or the like is provided along with the hydrophilic group can be advantageously used. Note that, while it is possible to combine use with a polyoxyalkylene-modified silicone, or an organopolyoxyalkylene group-containing surfactant, from the perspective of increasing environmental compatibility and changing the entire formulation of the cosmetic composition or the external use preparation to a PEG-FREE formulation, a non-polyether structure surfactant is preferably selected.

Depending on the intended use thereof, the cosmetic composition or external use preparation of the present invention can contain one or two or more polyhydric alcohols and/or lower monohydric alcohols as a component (G). These alcohols are the same as those disclosed by the applicants in paragraphs [0159] and [0160] and so on in the above-mentioned Patent Document 31 (WO 2011/049248).

However, from the perspective of increasing environmental compatibility and changing the entire formulation of the cosmetic composition or the external use preparation to a PEG-FREE formulation, a non-polyether structure polyhydric alcohol and/or lower monohydric alcohol is preferably selected.

Depending on the purpose thereof, the cosmetic composition or the external use preparation of the present invention can include one or two or more inorganic salts and/or organic salts as a component (H). These salts are the same as those disclosed by the applicants in paragraph [0161] and so on in the above-mentioned Patent Document 31 (WO 2011/049248).

Depending on the purpose thereof, the cosmetic composition or the external use preparation of the present invention can include at least one selected from the group consisting of a crosslinking organopolysiloxane, an organopolysiloxane elastomer spherical powder, a silicone resin, an acryl silicone dendrimer copolymer, a silicone raw rubber, a polyamide-modified silicone, an alkyl-modified silicone wax, and an alkyl-modified silicone resin wax as a component (I). These silicone-based components are the same as those disclosed by the applicants in paragraphs [0161] to [0193] and so on in the above-mentioned Patent Document 31 (WO 2011/049248).

Silicone polyether elastomer gels (J-1), such as the commercially available products Dow Corning EL-8050 ID SILICONE ORGANIC ELASTOMER BLEND, Dow Corning EL-8051 IN SILICONE ORGANIC ELASTOMER BLEND and Dow Corning EL-7040 HYDRO ELASTOMER BLEND, which exhibit improved compatibility with a variety of organic components and a stable thickening effect by introducing a polyoxypropylene group, as disclosed in WO 2007/109240 and WO 2009/006091, and the Pituitous Silicone Fluids (J-2) disclosed in WO 2011/028765 and WO 2011/028770 may be used as component (J) in the cosmetic composition or the external use preparation of the present invention depending on the intended use thereof. Furthermore, the liquid and slightly crosslinkable organopolysiloxane filed in Japan (as patent application 2010-289722) by the present applicant, and for which priority rights are claimed based on said application can be used in the present invention.

The cosmetic composition or the external use preparation of the present invention can, depending on the purpose of the cosmetic composition, include one or two or more water-soluble polymers as a component (K). These water-soluble polymers are the same as those disclosed by the applicants in paragraph [0201] and so on in the above-mentioned Patent Document 31 (WO 2011/049248). However, from the perspective of increasing environmental compatibility and changing the entire formulation of the cosmetic composition or the external use preparation to a PEG-FREE formulation, a non-polyether structure water-soluble polymer is preferably selected.

Depending on the purpose thereof, the cosmetic composition or the external use preparation of the present invention can include one or two or more ultraviolet light blocking components as a component (L). These ultraviolet light blocking components are the same as those disclosed by the applicants in paragraphs [0202] to [0204] and so on in the above-mentioned Patent Document 31 (WO 2011/049248). The ultraviolet light blocking components that can be used particularly preferably include at least one type selected from among the group comprising fine particulate titanium oxide, fine particulate zinc oxide, paramethoxy cinnamic acid 2-ethylhexyl, 4-tert-butyl-4'-methoxydibenzoylmethane, diethylamino hydroxybenzoyl hexyl benzoate, benzotriazole-based ultraviolet radiation absorbers, and triazine-based ultraviolet radiation absorbers such as 2,4,6-tris[4-(2-ethylhexyloxycarbonyl)anilino]1,3,5-triazine, and 2,4-bis-6-(4-methoxyphenyl)-1,3,5-triazine. These ultraviolet light blocking components are generally used, are easy to acquire, and have high ultraviolet light blocking effects and, thus can be beneficially used. In particular, using both inorganic and organic ultraviolet light blocking components is preferable, and using a UV-A blocking component in combination with a UV-B blocking component is more preferable.

By using an ultraviolet light blocking component in combination with a powder dispersing agent and an emulsifier for a water-in-oil emulsion that contains the aforementioned tri-block type co-modified organopolysiloxane in the cosmetic composition or the external use preparation of the present invention, it is possible to stably disperse the ultraviolet light blocking component in the cosmetic composition while improving the feeling to touch and storage stability of the overall cosmetic composition, and it is therefore possible to impart the cosmetic composition with excellent ultraviolet radiation blocking properties.

Various components other than the components described above can be used in the cosmetic composition or external use preparation of the present invention, provided that such use does not impair the effects of the present invention. Examples thereof include oil-soluble gelling agents, organo-modified clay minerals, preservatives, bioactive components, skin beautifying components, pH adjusting agents, antioxidants, solvents, chelating agents, moisturizing components, perfumes and the like. These optional components for cosmetic product are the same as those disclosed by the applicants in paragraphs [0207], [0208] and [0220] to [0228] and so on in the above-mentioned Patent Document 31 (WO 2011/049248).

Additionally, in cases where the external use preparation or the cosmetic composition according to the present invention is an anti-perspirant, or depending on the purpose thereof, the external use preparation or the cosmetic composition can contain an anti-perspiration active component and/or a deodorant agent. These anti-perspiration components and deodorant components are the same as those disclosed by the applicants in paragraphs [0209] to [0219] and so on in the above-mentioned Patent Document 31 (WO 2011/049248). Similarly, in cases where the external use preparation or the cosmetic composition according to the present invention is an anti-perspirant composition, the preparation and method of use of the various anti-perspirant compositions are the same as those disclosed by the applicants in paragraphs [0234] to [0275] and so on of the above-mentioned Patent Document 31 (WO 2011/049248).

INDUSTRIAL APPLICABILITY

An emulsifier for a water-in-oil emulsion or powder dispersing agent that contains the tri-block type co-modified organopolysiloxane of the present invention can be advantageously used as a raw material for an external use preparation or cosmetic composition. Furthermore, because of these excellent characteristics, the tri-block type co-modified organopolysiloxane of the present invention is line with the global trend of improving the constitution of an end consumer product such as a cosmetic product to a completely PEG-FREE formulation, and is a key material for providing a water-in-oil emulsion external use preparation or cosmetic composition which exhibits excellent stability, usability and feeling to touch despite not containing a compound having a polyoxyethylene moiety.

EXAMPLES

Hereinafter, the present invention is described in detail with reference to examples. It should be understood that the present invention is not restricted to the examples. Moreover, in the compositional formulae below, Me denotes a methyl ($-CH_3$) group, a $Me_3SiO$ group (or a $Me_3Si$ group) is represented by "M", a $Me_2HSiO$ group (or a $Me_2HSi$ group) is represented by "MH", a $Me_2SiO$ group is represented by "D", a MeHSiO group is represented by "$D^H$", and units in which methyl groups in M and D are modified by a substituent group are represented by "$M^R$" and "$D^R$". Additionally, in the production examples, "IPA" represents isopropyl alcohol.

Production Example 1 for Practical Examples

<Synthesis of Tri-Block Type Copolymer No. 1>
Step 1: 179.7 g of methylhydrogenpolysiloxane represented by the average composition formula $M^H D_{55} M^H$, and 13.9 g of 1-hexadecene (purity 91.7%) were placed in a reaction vessel, and 0.3 g of a hexamethyldisiloxane solution of a platinum-1,3-divinyl-1,1,3,3-tetramethyldisiloxane complex (platinum concentration 0.4 wt. %) was added under stirring at 25° C. under a nitrogen stream. The reaction liquid was heated to 60 to 80° C. and allowed to react for 7 hours, after which 2 g of sample was taken and it was confirmed by an alkali decomposition gas generation method that the target reaction rate had been achieved.
Step 2: 8.6 g of diglycerin monoallyl ether, 0.02 g of natural vitamin E and 60 g of IPA was added to the reaction liquid and allowed to react for 3.5 hours at 80° C., and it was confirmed that the reaction was complete through the method described above.
Step 3: 6 g of a 0.16% aqueous phosphoric acid solution and 3 g of purified water were added to the contents of the reaction vessel, and acid treatment was carried out for 3 hours under IPA reflux at 80 to 85° C. under stirring and under a nitrogen stream. The reaction liquid was then neutralized by adding 0.12 g of 2.5% aqueous ammonia, the IPA was distilled off under reduced pressure, and stripping was then carried out for 3.5 hours at a temperature of 80 to 100° C. and a pressure of 10 Torr so as to distill off low-boiling components. In this way, 198 g of a composition containing a tri-block type copolymer represented by the average composition formula $M^{R*11} D_{55} M^{R*22}$ was obtained as gray-brown homogeneous liquid.
In this formula, $R^{*11} = -C_{16}H_{33}$.
$R^{*22}$ is expressed by $-C_3H_6O-X$, where "X" is the diglycerin portion.

Production Example 2 for Practical Examples

<Synthesis of Tri-Block Type Copolymer No. 2>
Step 1: 178.9 g of methylhydrogenpolysiloxane represented by the average composition formula $M^H D_{55} M^H$ and 15.1 g of 1-hexadecene (purity 91.7%) were placed in a reaction vessel, and 0.3 g of a hexamethyldisiloxane solution of a platinum-1,3-divinyl-1,1,3,3-tetramethyldisiloxane complex (platinum concentration 0.4 wt. %) was added under stirring at 25° C. under a nitrogen stream. The reaction liquid was heated to 60 to 80° C. and allowed to react for 7 hours, after which 2 g of sample was taken and it was confirmed by an alkali decomposition gas generation method that the target reaction rate had been achieved.

Step 2: 10.5 g of a xylitol monoallyl ether (purity 84.4%), 0.02 g of natural vitamin E, and 60 g of IPA were added to the reaction liquid. Then, 0.1 g of the platinum catalyst solution described above was added. A reaction was allowed to occur for 14 hours at 65 to 80° C., and it was confirmed that the reaction was almost complete through the method described above.

Step 3: 6 g of a 0.16% aqueous phosphoric acid solution and 3 g of purified water were added to the contents of the reaction vessel, and acid treatment was carried out for 3 hours under IPA reflux at 80 to 85° C. under stirring and under a nitrogen stream. The reaction liquid was then neutralized by adding 0.13 g of 2.5% aqueous ammonia, the IPA was distilled off under reduced pressure, and stripping was then carried out for 1 hour at a temperature of 80 to 100° C. and a pressure of 10 Torr so as to distill off low-boiling components. In this way, 195 g of a composition containing a tri-block type copolymer represented by the average composition formula $M^{R*11}D_{55}M^{R*26}$ was obtained as an ash-white colored homogeneous liquid.

In this formula, $R^{*11}$=—$C_{16}H_{33}$.

$R^{*26}$ is expressed by —$C_3H_6O$—X, where "X" is the xylitol portion.

Production Example 1 for Comparative Examples

<Synthesis of Comparative Silicone Compound RE-1>

155.9 g of a methylhydrogenpolysiloxane expressed by the average composition formula $MD_{72}D^H{}_{12}M$, 13.0 g of a glycerin monoallyl ether represented by the structural formula $CH_2$=CH—$CH_2$—$OCH_2CH(OH)CH_2OH$, 41.1 g of 1-decene, and 63 g of IPA were placed in a reaction vessel, and heated to 45° C. while agitating under a nitrogen stream. 0.055 g of an IPA solution of a platinum-1,3-divinyl-1,1,3,3-tetramethyldisiloxane complex (Pt concentration=4.5 wt. %) was added thereto, and the mixture was reacted for one hour at 80° C. Then, 2 g of the reaction liquid was sampled, and it was confirmed that the reaction was complete through an alkali decomposition gas generation method. The reaction liquid was heated under reduced pressure so as to distill off low-boiling components. Thus, 195 g of a tan colored semi-transparent liquid composition comprising a monoglycerin derivative-modified silicone expressed by the average composition formula $MD_{72}D^{R*12}{}_9D^{R*21}{}_3M$ was obtained.

In this formula, $R^{*12}$=—$C_{10}H_{21}$.

$R^{*21}$=—$C_3H_6OCH_2CH(OH)CH_2OH$

Production Example 2 for Comparative Examples

<Synthesis of Comparative Silicone Compound RE-2>

134.6 g of a methylhydrogenpolysiloxane expressed by the average composition formula $MD_{72}D^H{}_{12}M$, 29.9 g of a polyglycerin monoallyl ether, 36.2 g of 1-decene, 200 g of IPA, and 0.25 g of a 2.3 wt. % sodium acetate/methanol solution were placed in a reaction vessel, and heated to 55° C. while agitating under a nitrogen stream. 0.16 g of an IPA solution having 5.0 wt. % of chloroplatinic acid was added, and the mixture was reacted for 7 hours at 80° C. Then, 2 g of the reaction liquid was sampled, and it was confirmed that the reaction was complete through an alkali decomposition gas generation method. The reaction liquid was heated under reduced pressure so as to distill off low-boiling components. Thus, 180 g of composition comprising a polyglycerin derivative-modified silicone expressed by the average composition formula $MD_{72}D^{R*12}{}_9D^{R*24}{}_3M$ was obtained. This composition had a gum-like form that was ash-white colored throughout and was not uniform but, rather, partial phase separation (of the gum-like tan colored phase) had occurred.

In this formula, $R^{*12}$=—$C_{10}H_{21}$.

$R^{*24}$ is expressed by —$C_3H_6O$—X, where "X" is the tetraglycerin portion.

Moreover, the polyglycerin monoallyl ether was synthesized by ring-opening polymerizing 3 mole equivalents of glycidol with 1 mole of a glycerin monoallyl ether, and had a structure in which an average of 4 moles of glycerin were added. Moreover, the glycerin monoallyl ether has two hydroxyl groups that can both react with the glycidol and the polyglycerin portion therefore includes not only a straight chain structure, but also a branched structure.

Production Example 3 for Comparative Examples

<Synthesis of Comparative Silicone Compound RE-3>

111.6 g of a methylhydrogenpolysiloxane expressed by the average composition formula $MD_{61}D^H{}_{15}M$ was placed in a reaction vessel. Then a mixture comprising 30.9 g of a single-terminal vinyl-modified dimethylpolysiloxane represented by the structural formula $CH_2$=$CHSiMe_2(OSiMe_2)_6OSiMe_3$ and 0.10 g of a toluene solution of a platinum-1,3-divinyl-1,1,3,3-tetramethyldisiloxane complex (Pt concentration: 0.5 wt. %) was added dropwise, and the mixture was agitated at room temperature, thereby obtaining a linear siloxane branched-type polysiloxane intermediate.

Additionally, 7.0 g of triglycerin monoallyl ether, 50.4 g of 1-dodecene, 100 g of IPA, and 0.40 g of an IPA solution of a platinum-1,3-divinyl-1,1,3,3-tetramethyldisiloxane complex (Pt concentration: 0.5 wt. %) were placed in another reaction vessel, and while agitating under a nitrogen stream, the mixture was added dropwise to the previously synthesized linear siloxane branched-type polysiloxane in refluxing solvent. After the adding was completed, heating and agitating was continued for 3 hours. Then, 2 g of the reaction liquid was sampled and it was confirmed that the reaction was complete through an alkali decomposition gas generation method.

Next, the reaction liquid was moved to an autoclave and 4.0 g of a sponge nickel catalyst, 2.0 g of water, and 2.0 g of IPA was added. Then, hydrogen gas was introduced and hydrogenation treatment was carried out for 6 hours under the following conditions: 110° C., 0.9 MPa. The reaction mixture was cooled to 60° C. after the treatment and blown with hydrogen gas. Then, purging with nitrogen gas was performed three times. Next, the sponge nickel catalyst was removed via precision filtration. Thus, 204 g of a colorless, transparent filtrate was obtained.

This filtrate was placed in a separate reaction vessel and maintained for one hour at 100° C. and 20 Torr under a nitrogen stream so as to distill off low-boiling components. Thus, 138 g of a substantially colorless, semi-transparent and uniform liquid composition comprising a triglycerin derivative-modified silicone expressed by the average composition formula $MD_{61}D^{R*13}{}_{12}D^{R*32}{}_2D^{R*23}{}_1M$ was obtained.

In this formula, $R^{*13}$=—$C_{12}H_{25}$ $R^{*32}$=—$C_2H_4SiMe_2(OSiMe_2)_6OSiMe_3$ $R^{*23}$=—$C_3H_6O$—X, where X is the triglycerin moiety.

Production Example 4 for Comparative Examples

<Synthesis of Comparative Silicone Compound RE-4>

Step 1: 106.0 g of a methylhydrogenpolysiloxane expressed by the average composition formula $MD_{37}D^H{}_{13}M$, and 9.3 g of a vinyl tris(trimethylsiloxy)silane expressed by the average composition formula $CH_2=CH-Si(OSiMe_3)_3$ were placed in a reaction vessel. Then, 0.26 g of an IPA solution of a platinum-1,3-divinyl-1,1,3,3-tetramethyldisiloxane complex (Pt concentration: 0.4 wt. %) was added at room temperature while agitating under a nitrogen stream. The mixture was reacted for one hour while heating in an oil bath set to a temperature of 68° C. Then, 2 g of the reaction liquid was sampled and it was confirmed that the reaction rate was not in error through an alkali decomposition gas generation method.

Step 2: 26.6 g of 1-dodecene was added to the reaction liquid and the heat generated thereby caused the temperature to rise from 35° C. to 61° C. While heating using an oil bath set to 65° C., a reaction was allowed to occur for 1.5 hours, and it was then confirmed that there were no problems in terms of reaction rate in the same way as above.

Step 3: 31.5 g of polyoxyethylene(10)monoallyl ether, 0.02 g of natural vitamin E, and 60 g of IPA were added to the reaction liquid. Then, 0.25 g of the platinum catalyst solution described above was added. The temperature rose about 4° C. due to the generated heat. A reaction was allowed to occur for 1 hour under the conditions described above, and it was then confirmed that there were no problems in terms of reaction rate in the same way as above.

Step 4: 26.6 g of 1-dodecene was added to the reaction liquid and the heat generated thereby caused the temperature to rise about 8° C. The mixture was reacted for 1.5 hours while heating in an oil bath set to a temperature of 65° C. and, thereafter, it was confirmed that the reaction was complete. Thereafter, the reaction liquid was heated under reduced pressure to remove low-boiling components by distillation.

Step 5: An aqueous solution obtained by dissolving 0.03 g of sodium hydrogensulfate monohydrate in 3 g of purified water was added to the contents of the reaction vessel, and acid treatment was carried out for 30 minutes at 70 to 80° C. under stirring and under a nitrogen stream. After distilling off water and low-boiling components at 70° C. under reduced pressure, the pressure was restored when water droplets in the system had disappeared (first acid treatment). Next, 3 g of water was added and treatment was carried out in the same way for 1 hour, water and other low-boiling components were distilled off, and the pressure was restored when water droplets in the system had disappeared (second acid treatment). After carrying out the same procedure again (third acid treatment), ultrafiltration was carried out so as to obtain 149 g of a composition containing a polyether-modified silicone represented by the average composition formula $MD_{37}D^{R*13}{}_{10}D^{R*31}{}_{1}D^{R*25}{}_{2}M$ as a tan colored clear homogeneous liquid.

In this formula, $R^{*13}=-C_{12}H_{25}$
$R^{*31}=-C_2H_4Si(OSiMe_3)_3$
$R^{*26}=-C_3H_6O(C_2H_4O)_{10}H$ Production Example 5 for Comparative Examples <Synthesis of Comparative Silicone Compound RE-5>
224.6 g of a methylhydrogenpolysiloxane represented by the average composition formula $MD_{70}D^H{}_3M$, 30.5 g of xylitol monoallyl ether (purity 92.3%), 0.25 g of a 2.3% methanol solution of sodium acetate and 75.0 g of IPA were placed in a reaction vessel, heated under stirring and under a nitrogen stream, and 0.18 g of a 10% IPA solution of chloroplatinic acid was added at 45° C. A reaction was allowed to occur for 6.5 hours at 45 to 80° C., after which 2 g of the reaction liquid was sampled and it was confirmed that the reaction was complete through an alkali decomposition gas generation method. Low-boiling components were distilled off by heating the reaction liquid under reduced pressure so as to obtain 215 g of a sugar alcohol-modified silicone represented by the average composition formula $MD_{70}D^{R*26}{}_3M$ as a light yellow colored, opaque homogeneous viscous liquid.
In the formula, $R^{*26}=-C_3H_8O-X$, and X is a xylitol moiety Production Example 6 for Comparative Examples <Synthesis of Comparative Silicone Compound RE-6>

Step 1: 365.4 g of a methylhydrogenpolysiloxane represented by the average composition formula $M^H D_{55} M^H$ and 17.5 g of 1-dodecene were placed in a reaction vessel, and 0.5 g of an IPA solution of a platinum-1,3-divinyl-1,1,3,3-tetramethyldisiloxane complex (platinum concentration 0.4 wt. %) was added under stirring at 25° C. under a nitrogen stream. The reaction liquid was heated to 70° C. and allowed to react for 1 hour, after which 2 g of sample was taken and it was confirmed by an alkali decomposition gas generation method that the target reaction rate had been achieved.

Step 2: 19.1 g of xylitol monoallyl ether (purity 91.3%), 0.04 g of natural vitamin E, and 280 g of IPA were added to the reaction liquid. Then, 1.0 g of the platinum catalyst solution described above was added. A reaction was allowed to occur for 2.5 hours at 50 to 70° C., and it was confirmed that the reaction was almost complete through an alkali decomposition gas generation method.

Step 3: After distilling off the IPA under reduced pressure, an aqueous solution obtained by dissolving 0.02 g of sodium hydrogensulfate monohydrate in 6 g of purified water was added to the contents of the reaction vessel, and acid treatment was carried out for 45 minutes at 65 to 70° C. under stirring and under a nitrogen stream. Water and low-boiling components were distilled off at 70° C. under reduced pressure, and the pressure was restored when the distillation stopped (first acid treatment). Next, 6 g of water was added, water and other low-boiling components were distilled off in the same way, and the pressure was restored when the distillation stopped (second acid treatment). After carrying out the same procedure again (third acid treatment), water droplets in the system were removed by maintaining a temperature of 65 to 70° C. for 2 hours under reduced pressure, and the pressure was then restored. Ultrafiltration was carried out so as to obtain 337 g of a composition containing tri-block type copolymer represented by the average composition formula $MR^{*13}D_{55}M^{R*26}$ as a light yellowish-brown, clear, homogeneous liquid.

In this formula, $R*^{13}=\text{—}C_{12}H_{25}$
$R*^{26}$ is expressed by —$C_3H_6O$—X, where "X" is the xylitol portion.

The average composition formulae of tri-block type copolymer No. 1 and No. 2 according to the present invention, and Comparative Silicone Compound RE-1 to Comparative Silicone Compound RE-6 according to the comparative examples, which were synthesized according to the methods described above, are as follows.

TABLE 1

| Silicone compound | Average composition formula of modified silicone compound | Properties |
|---|---|---|
| Tri-block type copolymer No. 1 | $M^{R*11}D_{55}M^{R*22}$ (Tri-block type diglycerin-modified) | Gray-brown, homogeneous liquid |
| Tri-block type copolymer No. 2 | $M^{R*11}D_{55}M^{R*26}$ (Tri-block type xylitol-modified) | Ash-white colored, homogeneous liquid |
| Comparative silicone compound RE-1 | $MD_{72}D^{R*12}{}_9D^{R*21}{}_3M$ (Side chain type monoglycerin-modified) | Tan colored, semi-transparent liquid |
| Comparative silicone compound RE-2 | $MD_{72}D^{R*12}{}_9D^{R*24}{}_3M$ (Side chain type polyglycerin-modified) | Ash-white gum (partial phase separation) |
| Comparative silicone compound RE-3 | $MD_{61}D^{R*13}{}_{12}D^{R*32}{}_2D^{R*23}{}_1M$ (Side chain type triglycerin-modified) | Substantially colorless, semi-transparent, homogeneous liquid |
| Comparative silicone compound RE-4 | $MD_{37}D^{R*13}{}_{10}D^{R*31}{}_1D^{R*31}{}_1D^{R*25}{}_2M$ (Side chain type polyether-modified) | Tan colored, clear, homogeneous liquid |
| Comparative silicone compound RE-5 | $MD_{70}D^{R*26}{}_3M$ (Side chain type xylitol-modified) | Light yellow colored, opaque homogeneous viscous liquid |
| Comparative silicone compound RE-6 | $M^{R*13}D_{55}M^{R*26}$ (Tri-block type xylitol-modified) | Light yellowish-brown, clear, homogeneous liquid |

In the tables, the structures and types of the functional groups are as follows.
<Siloxane branch group: $R*^3$>
$R*^{31}=\text{—}C_2H_4Si(OSiMe_3)_3$
$R*^{32}=\text{—}C_2H_4SiMe_2(OSiMe_2)_6OSiMe_3$
<Hydrophilic group: $R*^2$>
$R*^{21}=\text{—}C_3H_6OCH_2CH(OH)CH_2OH$
$R*^{22}=\text{—}C_3H_6O$—X, where "X" is the diglycerin portion.
$R*_{23}=\text{—}C_3H_6O$—X, where X is the triglycerin portion.
$R*^{24}=\text{—}C_3H_6O$—X, where X is the tetraglycerin portion.
$R*^{25}=\text{—}C_3H_6O(C_2H_4O)_{10}H$
$R*^{26}=\text{—}C_3H_6O$—X, where "X" is the xylitol portion.
<Other hydrophobic organic group: $R*^1$>
$R*^{11}=\text{—}C_{16}H_{33}$
$R*^{12}=\text{—}C_{10}H_{21}$
$R*^{13}=\text{—}C_{12}H_{25}$ Practical Examples 1 to 6 and Comparative Examples 1 to 18

Using the silicone compounds obtained in Production Examples 1 and 2 for practical examples and Production Examples 1 to 6 for comparative examples, water-in-oil emulsion compositions having the formulations shown in Table 2 to Table 4 were prepared as described below. These compositions were evaluated in terms of viscosity stability and emulsion particle diameter stability according to the evaluation criteria below. The results are shown in Tables 2 and 3. In the table, "parts" indicates "parts by weight (mass)".

Preparation method for water-in-oil emulsion composition
1. A silicone compound comprising an oil agent and a surfactant was placed in a 200 mL container.
2. The compound was agitated and the surfactant was uniformly dispersed or dissolved in the oil agent (oil phase A).
3. Table salt and ion exchanged water were placed in a separate container. The salt was dissolved by mixing using a spatula. Furthermore, 1,3-butylene glycol was mixed and dissolved therein (aqueous phase B).
4. The saw teeth of the homo-disper were immersed in the oil phase A and, the aqueous phase B was poured into the oil phase A at a constant rate over a period of about 45 seconds, while agitating at 1,000 rpm.
5. The rotational speed of the homo-disper was increased to 3500 rpm, and the contents were homogeneously emulsified by stirring for 2 minutes.
6. Agitation was stopped. Then, the oily component adhered to the inner wall of the container was scraped off using a spatula and mixed with the produced emulsion.
7. The contents were homogeneously emulsified by stirring for 3 minutes with the rotational speed of the homo-disper at 3500 rpm.

Evaluation of Viscosity Stability 28 g of each water-in-oil emulsion composition was measured into a 35 mL glass bottle. The bottles were capped and allowed to sit at rest in a 50° C. constant temperature bath for one month.
The viscosity stability of the emulsions before and after sitting was evaluated according to the following standards.
●: Viscosity variation=<±10% and appearance was uniform without change
○: ±10%<viscosity variation=<±20% and appearance was uniform
Δ: ±20%<viscosity variation=<±30%, or slight decrease in uniformity of the surface of the emulsion.
x: ±30%<viscosity variation, or separation of water drops, aqueous phase, oil phase, or the like.

(Cases where the emulsifying itself was not possible are also indicated as "x")

Measurement of emulsified particle size and evaluation of stability

Observations and photographs using an optical microscope (at a magnification of 1000 times) were taken on the day after the water-in-oil emulsion compositions were prepared and after allowing the emulsion compositions (after sealing 28 g of the composition in a 35 mL glass bottle, as described above) to stand for 1 month at 50° C., and the weight average particle diameter was calculated using image analysis software. Thereby, stability was evaluated by examining the initial emulsified particle size and the emulsified particle size over time.

Note that notes were made in the Tables when particle coalescence was observed.
- ●: Change in emulsified particle size was small, and signs of coalescence were absent.
- ○: The emulsified particle size potentially increased slightly but definite coalescence was not observed. Alternatively, the emulsified particle size increased, but the overall particle size was small and the emulsion system was maintained.
- Δ: It is thought that partial coalescence of the particles occurred. Definite increase in the maximum emulsified particle size.
- x: Many particles were coalesced and emulsion was in the state of breaking down. (Cases where the emulsifying itself was not possible are also indicated as "x")

TABLE 2 water-in-oil emulsion composition formulations and evaluation results
(Practical Examples 1 to 6 and Comparative Examples 1 to 3)

| Name of raw material | Practical Examples | | | | | | Comparative Examples | | |
|---|---|---|---|---|---|---|---|---|---|
| | 1 | 2 | 3 | 4 | 5 | 6 | 1 | 2 | 3 |
| Tri-block type copolymer No. 1 | 2 | 2 | 2 | — | — | — | — | — | — |
| Tri-block type copolymer No. 2 | — | — | — | 2 | 2 | 2 | — | — | — |
| Comparative silicone compound RE-1 | — | — | — | — | — | — | — | — | — |
| Dimethylpolysiloxane (6 cSt) | 23 | 11.5 | — | 23 | 11.5 | — | 23 | 11.5 | — |
| Mineral oil 50SUS (37.8° C.) | — | 11.5 | 23 | — | 11.5 | 23 | — | 11.5 | 23 |
| Sodium chloride | 0.5 | 0.5 | 0.5 | 0.5 | 0.5 | 0.5 | 0.5 | 0.5 | 0.5 |
| Purified water | 68.5 | 68.5 | 68.5 | 68.5 | 68.5 | 68.5 | 68.5 | 68.5 | 68.5 |
| 1,3-butylene glycol | 6 | 6 | 6 | 6 | 6 | 6 | 6 | 6 | 6 |
| Viscosity stability of emulsion | ○ | ○ | ○ | ● | ● | ● | X | X | X |
| Initial particle diameter (μm) | 3 | 3 | 3 | 3 | 3 | 3 | Separated | Separated | Separated |
| Particle diameter (μm) after 1 month at 50° C. | 3 | 3 | 3 | 3 | 3 | 3 | Separated | Separated | Separated |
| Stability of emulsified particles | ● | ● | ● | ● | ● | ● | X | X | X |

TABLE 3 water-in-oil emulsion composition formulations and evaluation results
(Comparative Examples 4 to 12)

| Name of raw material | Comparative Examples | | | | |
|---|---|---|---|---|---|
| | 4 | 5 | 6 | 7 | 8 |
| Comparative silicone compound RE-2 | 2 | 2 | 2 | — | — |
| Comparative silicone compound RE-3 | — | — | — | 2 | 2 |
| Comparative silicone compound RE-4 | — | — | — | — | — |
| Dimethylpolysiloxane (6 cSt) | 23 | 11.5 | — | 23 | 11.5 |
| Mineral oil 50SUS (37.8° C.) | — | 11.5 | 23 | — | 11.5 |
| Sodium chloride | 0.5 | 0.5 | 0.5 | 0.5 | 0.5 |
| Purified water | 68.5 | 68.5 | 68.5 | 68.5 | 68.5 |
| 1,3-butylene glycol | 6 | 6 | 6 | 6 | 6 |
| Viscosity stability of emulsion | ○ | x | x | ● | ● |
| Initial particle diameter (μm) | 5 | 5 (coalesced) | 4 | 4 | 4 (coalesced) |
| Particle diameter (μm) after 1 month at 50° C. | 5 (coalesced) | Separated | Separated | 5 | 5 (coalesced) |

TABLE 3-continued water-in-oil emulsion composition formulations and evaluation results
(Comparative Examples 4 to 12)

| Stability of emulsified particles | ○ | x | x | ○ | Δ |
|---|---|---|---|---|---|

| Name of raw material | Comparative Examples | | | |
|---|---|---|---|---|
| | 9 | 10 | 11 | 12 |
| Comparative silicone compound RE-2 | — | — | — | — |
| Comparative silicone compound RE-3 | 2 | — | — | — |
| Comparative silicone compound RE-4 | — | 2 | 2 | 2 |
| Dimethylpolysiloxane (6 cSt) | — | 23 | 11.5 | — |
| Mineral oil 50SUS (37.8° C.) | 23 | — | 11.5 | 23 |
| Sodium chloride | 0.5 | 0.5 | 0.5 | 0.5 |
| Purified water | 68.5 | 68.5 | 68.5 | 68.5 |
| 1,3-butylene glycol | 6 | 6 | 6 | 6 |
| Viscosity stability of emulsion | x | ● | ● | ● |
| Initial particle diameter (μm) | 4 | 3 | 3 | 3 |
| Particle diameter (μm) after 1 month at 50° C. | Separated | 3 | 3 | 3 |
| Stability of emulsified particles | x | ● | ● | ● |

TABLE 4 water-in-oil emulsion composition formulations and
evaluation results (Comparative Examples 13 to 18)

| Name of raw material | Comparative Examples | | | | | |
|---|---|---|---|---|---|---|
| | 13 | 14 | 15 | 16 | 17 | 18 |
| Comparative silicone compound RE-5 | 2 | 2 | 2 | — | — | — |
| Comparative silicone compound RE-6 | — | — | — | 2 | 2 | 2 |
| Dimethylpolysiloxane (6 cSt) | 23 | 11.5 | — | 23 | 11.5 | — |
| Mineral oil 50SUS (37.8° C.) | — | 11.5 | 23 | — | 11.5 | 23 |
| Sodium chloride | 0.5 | 0.5 | 0.5 | 0.5 | 0.5 | 0.5 |
| Purified water | 68.5 | 68.5 | 68.5 | 68.5 | 68.5 | 68.5 |
| 1,3-butylene glycol | 6 | 6 | 6 | 6 | 6 | 6 |
| Viscosity stability of emulsion | Δ | X | X | Δ | Δ | X |
| Initial particle diameter (μm) | 3 | 4 | 5 | 4 | 4 (coalesced) | 5 |
| Particle diameter (μm) after 1 month at 50° C. | 3 | Separated | Separated | 5 | 5 (coalesced) | Separated |
| Stability of emulsified particles | ● | X | X | ○ | Δ | X |

From the results above, it is clear that only the above-mentioned tri-block type copolymer No. 1 and No. 2 (emulsifiers for a water-in-oil emulsion containing the tri-block type copolymer of the present invention) exhibited similar or superior emulsification performance to comparative silicone compound RE-4, which is a polyether-modified silicone, of the various hydrophilic silicones that were tested.

Functionality Evaluation (Tactile Sensation and Sensation During Use)

Next, the water-in-oil emulsion compositions of Practical Example 3 and Practical Example 6, which achieved good results in the aforementioned stability test, and the water-in-oil emulsion composition of Comparative Example 12 were compared in terms of feeling to touch when used as cosmetic compositions. Specifically:

1. 0.20 g of the water-in-oil emulsion composition was placed on a finger and spread on the back of the hand.
2. In this case, 1) spreadability and smoothness when applying to during application, 2) lack of oiliness during application to after application, 3) lack of film sensation (stickiness when dry) after application, and 4) durability of moisturizing feel were evaluated according to the following standards.

Spreadability and smoothness: Applying to during application
●: Smooth tactile sensation and spreads easily without effort
○: Smooth tactile sensation and spreads easily
Δ: Initial smoothness is experienced, but spreadability is lacking. Resistance (stickiness and adhesion when dry) with progressive spreading is experienced.
x: Heavy, poor spreadability or noticeable stickiness when initially applied.

Lack of oiliness: During application to after application
●: A pleasant, water-like tactile sensation that lasts until the latter part of application. Because oiliness is controlled in order to obtain an excellent moisturizing feel, an extremely natural sensation during use with no discomfort in terms of appearance or sensation can be obtained.
○: While fading out from during application to after application, a wet (water-like) tactile sensation remains in trace amounts. Thus, a tactile sensation in which oiliness is balanced is obtained.
Δ: While a wet tactile sensation is experienced during initial application, this sensation disappears quickly and oiliness becomes predominant.
x: Tactile sensation is oily from initial application and the surface of the skin appears very oily.

Lack of film sensation: After application
●: Nearly no sensation of stickiness (film sensation) when dry
○: Slight sensation of stickiness (film sensation) when dry
Δ: Stickiness (film sensation) when dry experienced
x: Strong, unpleasant sensation of stickiness at latter part of application Durability of moisturizing feel: 10 minutes after application
●: Luxurious moisturizing feel lasted and there is a natural feeling with no discomfort
○: Moisturizing feel remains, but skin feels slightly drier than immediately after application. Some oiliness is visible.
Δ: No moisturizing feel and oily shine is noticeable.
x: Discomfort and irritation of the skin due to drying is felt sifiers, and could maintain moisture retention after application despite having the unique characteristic of not causing stickiness.

Therefore, an emulsifier for a water-in-oil emulsion that contains the tri-block type copolymer of the present invention exhibits the excellent W/O emulsification performance shown in Table 2 and the excellent effect as a feeling to touch improvement agent or moisturizing agent shown in Table 5, and has therefore been verified as being extremely useful as a raw material for an external use preparation or cosmetic composition. An emulsifier for a water-in-oil emulsion or a powder dispersing agent that contains the tri-block type copolymer of the present invention can be advantageously used as a raw material for an external use preparation or cosmetic composition and because of these excellent characteristics, is in line with the global trend of improving the constitution of an end consumer product such as a cosmetic product to a completely PEG-FREE formulation, and can produce a water-in-oil emulsion external use preparation or cosmetic composition that exhibits excellent stability, usability and feeling to touch despite not containing a compound having a polyoxyethylene moiety.

Hereinafter, formulation examples of the cosmetic composition and the external use preparation according to the present invention are described, but it is understood that the cosmetic composition and the external use preparation according to the present invention are not limited to the types and compositions recited in these formulation examples.

Formulations Already Disclosed in Previous Applications
The tri-block type copolymer according to the present invention can be used in a variety of external use preparations and cosmetic compositions. Specific formulation examples thereof include those obtained by replacing components corresponding to silicone compounds No. 1 to No. 16 in the various external use preparation and cosmetic composition formulations disclosed by the applicants in the practical examples and so on in the above-mentioned Patent Document 31 (WO 2011/049248) with the above-mentioned tri-block type copolymer according to the present invention

TABLE 5

Functional evaluation results of water-in-oil emulsion compositions (Practical Example 3, Practical Example 6 and Comparative Example 12)

| Technical classification | Emulsifier | Feeling to touch and feeling of use | | | |
| --- | --- | --- | --- | --- | --- |
| | | Smoothness/ spreadability | Suppression of oiliness | Lack of film sensation | Moisturizing feel durability |
| Practical Example 3 | Tri-block type copolymer No. 1 | ● | ● | ● | ● |
| Practical Example 6 | Tri-block type copolymer No. 2 | ● | ○ | ○ | ○ |
| Comparative Example 12 | Comparative silicone compound RE-4 | ● | Δ | ○~Δ | Δ |

From the results above, it is clear that water-in-oil emulsion compositions that contain the above-mentioned tri-block type copolymer No. 1 and No. 2 (emulsifiers for a water-in-oil emulsion containing the tri-block type copolymer of the present invention) were comprehensively superior to a water-in-oil emulsion composition that contains comparative silicone compound RE-4, which is a polyether-modified silicone, in terms of feeling to touch and feeling of use, could sustainably suppress oiliness, which has long been a problem with W/O formulations, while being emul- (for example, the tri-block type copolymer No. 1 and/or No. 2), and such examples are encompassed by the scope of the invention of the present application as formulation examples of the cosmetic composition or external use preparation according to the present invention.

In addition, formulations obtained by replacing components corresponding to silicone compounds No. 1 to No. 16 in the various external use preparation and cosmetic composition formulations disclosed by the applicants in the practical examples and so on in the above-mentioned Patent Document 31 (WO 2011/049248) with the above-mentioned tri-block type copolymer according to the present invention (for example, the tri-block type copolymer No. 1 and/or No. 2) and, in cases where compounds containing a polyoxyethylene group or polyoxyethylene moiety are used in the formulation, replacing these compounds with arbitrary non-PEG structure replacement materials are encompassed by the scope of the invention of the present application as formulation examples of the cosmetic composition or external use preparation according to the present invention. For example, it is possible to design a PEG-FREE formulation by replacing said materials with a PEG-FREE hydrophilic silicone such as a diglycerin-modified silicone and sugar alcohol-modified silicone in a composition that uses a polyether-modified silicone in said formulation examples.

Specifically, the practical examples and so on in the above-mentioned Patent Document 31 disclose milky lotions, lip glosses, oil-based foundations, water-in-oil emulsion transparent anti-perspirant compositions and non-aqueous stick-form anti-perspirant compositions as compositions able to be replaced by the tri-block type co-modified organopolysiloxane according to the present invention, and paragraphs [0459] to [0501] in the above-mentioned Patent Document 31 also disclose the following formulation examples. By using the tri-block type co-modified organopolysiloxane of the present invention, the stability over time and stability to heat is further improved in the case of a W/O emulsion. In addition, because the tri-block type co-modified organopolysiloxane of the present invention has excellent compatibility with not only silicone oils, but also a wide range of organic oils, homogeneity and compounding stability is further improved in non-aqueous formulations and powder-containing formulations, and the effect and quality of cosmetic compositions is therefore increased.

Example 1: Emulsion foundation
Example 2: Liquid foundation
Example 3: Foundation
Example 4: Water-in-oil cream
Example 5: Water-in-oil emulsion composition
Example 6: Water-in-oil emulsion lipstick (liquid)
Example 7: Liquid rouge
Example 8: Rouge
Example 9: Sunscreen emulsion
Example 10: Emulsion
Example 11: UV blocking cream
Example 12: UV blocking water-in-oil emulsion
Example 13: Sunscreen agent
Example 14: Water-in-oil emulsion sunscreen
Example 15: O/W cream
Example 16: Eye shadow
Example 17: Mascara
Example 18: Mascara
Example 19: Solid powder eye shadow
Example 20: Pressed powder cosmetic
Example 21: Powder foundation
Example 22: Pressed foundation
Example 23: Cream
Example 24: Foundation
Example 25: Water-in-oil emulsion-type sunscreen
Example 26: Lipstick
Example 27: Rouge
Example 28: Foundation
Example 29: Anti-perspirant aerosolized cosmetic composition
Example 30: Nonaqueous pressurized anti-perspirant product
Example 31: Aerosol type anti-perspirant composition
Example 32: Anti-perspirant lotion composition
Example 33: W/O: emulsion-type skin external use preparation
Example 34: Nonaqueous anti-perspirant deodorant stick composition
Example 35: W/O solid anti-perspirant stick composition
Example 36: W/O: emulsion type anti-perspirant cream composition
Example 37: Mascara
Example 38: Aftershave cream
Example 39: Solid foundation
Example 40: Daytime use skin-lightening cream
Example 41: Sun tanning cream
Example 42: Polyol/O-type nonaqueous emulsion skin external use preparation
Example 43: Polyol/O-type nonaqueous emulsion skin external use preparation In addition, formulations obtained by replacing the sugar alcohol-modified silicones 1 and 2 or the co-modified silicones 1 and 2 in the various external use preparation and cosmetic composition formulations disclosed by the applicants in the practical examples and so on in the above-mentioned Patent Documents 42 (WO 2011/136397) and 43 (WO 2011/049246) with the above-mentioned tri-block type copolymer according to the present invention (for example, the tri-block type copolymer No. 1 and/or No. 2) and, in cases where compounds containing a polyoxyethylene group or polyoxyethylene moiety are used in the formulation, replacing these compounds with arbitrary non-PEG structure replacement materials are encompassed by the scope of the invention of the present application as formulation examples of the cosmetic composition or external use preparation according to the present invention. For example, it is possible to design a PEG-FREE formulation by replacing said materials with a PEG-FREE hydrophilic silicone such as a diglycerin-modified silicone and sugar alcohol-modified silicone in a composition that uses a polyether-modified silicone in said formulation examples.

Specifically, paragraphs [0213] to [0251] in the above-mentioned Patent Document 42 disclose the following practical examples as compositions in which replacement with the tri-block type copolymer according to the present invention can be carried out.

Example 9, 10: Liquid foundation
Example 11: Sunscreen cosmetic composition
Example 12: Liquid foundation
Example 13: Oil-based mascara
Example 14: Lip gloss In addition, paragraphs [0196] to [0237] in Patent Document 43 disclose the following practical examples as compositions in which replacement with the tri-block type copolymer according to the present invention can be carried out.

Examples 3 and 4: Sun-screen agents (shaking type)
Example 5: W/O type foundation (gel-like)
Example 6: W/O type foundation (liquid type)
Example 7: Mascara
Example 8: Foundation cream
Example 9: Lip gloss
Example 10: Rouge
Example 11: Sun-screen cream (W/O type)

By using the tri-block type copolymer of the present invention, the stability over time and stability to heat is further improved in the case of a W/O emulsion. In addition, because the tri-block type copolymer of the present invention has excellent compatibility with not only silicone oils, but also a wide range of organic oils, homogeneity and compounding stability is further improved in non-aqueous formulations and powder-containing formulations, and the effect and quality of cosmetic compositions is therefore increased.

Other Formulations

In addition, it is possible to design the following hydrocarbon-based cosmetic base material as a completely PEG-FREE formulation by using, for example, the tri-block type copolymer No. 1

(Practical Example 1) of the Present Invention

Formulation example: Liquid foundation (W/O)

(Components)

| | | |
|---|---|---|
| 1. Isododecane | 20 | parts |
| 2. Isohexadecane | 10 | parts |
| 3. Isotridecyl isononanoate | 3 | parts |
| 4. Glyceryl tricapryl-caprate | 2 | parts |
| 5. Tri-block type copolymer No. 1 | 2.0 | parts |
| 6. Organo-modified clay mineral (Bentone 38V) | 1.5 | parts |
| 7. Octyl methoxycinnamate | 5 | parts |
| 8. Octylsilane treated titanium oxide | 8.5 | parts |
| 9. Octylsilane treated red iron oxide | 0.4 | parts |
| 10. Octylsilane treated yellow iron oxide | 1 | part |
| 11. Octylsilane treated black iron oxide | 0.1 | parts |
| 12. Dimethicone, dimethicone crosspolymer*[1] | 2 | parts |
| 13. Isododecane/(acrylates/polytrimethylsiloxy methacrylate) copolymer*[2] | 1 | part |
| 14. Trimethylsiloxysilicate | 1 | part |
| 15. 1,3-butylene glycol | 5 | parts |
| 16. Glycerin | 3 | parts |
| 17. Sodium chloride | 0.5 | parts |
| 18. Preservative | q.s. | |
| 19. Purified water | remainder | |
| 20. Perfume | q.s. | |

Note
*[1]DC9045, manufactured by Dow Corning

Note
*[2]FA-4002ID, manufactured by Dow Corning Toray Co., Ltd.

Production Method

Step 1: Components 1, 2, 5, 6, 7, 12, 13 and 14 are agitated and mixed.

Step 2: Components 3, 4 and 8 to 11 are kneaded and mixed using a three-roll mill.

Step 3: While agitating, the compound of Step 2 is added to the compound obtained in Step 1 and agitated and mixed further.

Step 4: An aqueous phase formed by uniformly dissolving components 15 to 20 is added to the mixture obtained in Step 3, emulsified, and a container is filled with the emulsion. Thus, a product is obtained.

The obtained W/O type liquid foundation has no unpleasant odor, has excellent emulsion stability when used, has excellent moisture resistance and cosmetic durability, has excellent texture, masks wrinkles, has a light feeling to touch and has excellent adhesion.

The invention claimed is:

1. A co-modified organopolysiloxane of General Formula (1) below and which does not comprise an oxyalkylene structure having an average number of repetitions of an oxyalkylene unit of two or higher in the molecule:

General Formula (1)

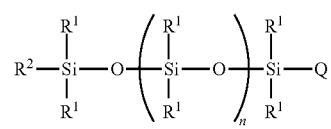

(1)

wherein, the $R^1$ groups are each independently a substituted or unsubstituted monovalent hydrocarbon group having 1 to 12 carbon atoms, excluding a group having an oxyalkylene structure having an average number of repetitions of an oxyalkylene unit of two or higher, $R^2$ is a substituted or unsubstituted monovalent hydrocarbon group having 13 to 30 carbon atoms, excluding a group having an oxyalkylene structure having an average number of repetitions of an oxyalkylene unit of two or higher, Q is a sugar alcohol group-containing organic group, excluding a group having an oxyalkylene structure having an average number of repetitions of an oxyalkylene unit of two or higher, or a glycerin derivative group having an average number of repetitions of a glycerin unit of 1.1 to 2.9, excluding a group having an oxyalkylene structure having an average number of repetitions of an oxyalkylene unit of two or higher; and n is a number in a range of 0 to 100.

2. The co-modified organopolysiloxane according to claim 1, wherein, in General Formula (1), Q is a diglycerin derivative group-containing organic group, excluding a group having an oxyalkylene structure having an average number of repetitions of an oxyalkylene unit of two or higher, which comprises 1.5 to 2.4 repeating units of one or more glycerin units selected from among the sugar alcohol group-containing organic groups of Structural Formulae (3-1) to (3-2) below or the glycerin units of Structural Formulae (4-1) to (4-3) below and which is bonded to a silicon atom via a linking group that is at least divalent, excluding a group having an oxyalkylene structure having an average number of repetitions of an oxyalkylene unit of two or higher:

Structural Formulae (3-1) to (3-2)

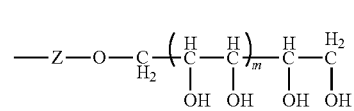

(3-1)

wherein, Z is a divalent organic group, excluding a group having an oxyalkylene structure having an average number of repetitions of an oxyalkylene unit of two or higher, and m is 1 or 2;

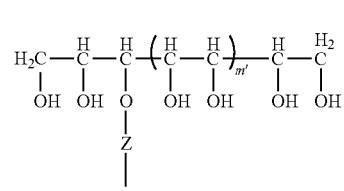

(3-2)

wherein, Z is as defined above, and m' is 0 or 1;

(4-1)

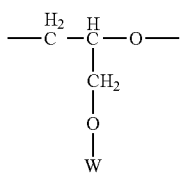

wherein, W is a hydrogen atom or an alkyl group having from 1 to 20 carbon atoms;

(4-2)

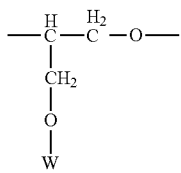

wherein, W is as defined above; and (4-3)

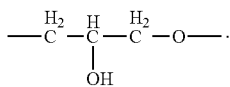

3. The co-modified organopolysiloxane according to claim 1, wherein the diglycerin derivative group-containing organic group comprises a diglycerin derivative group-containing organic group of General Formula (5-1) below:

(5-1)

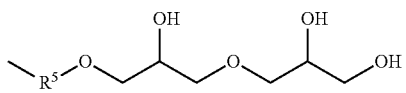

wherein, $R^5$ is a divalent organic group, excluding a group having an oxyalkylene structure having an average number of repetitions of an oxyalkylene unit of two or higher, or General Formula (5-2) below:

(5-2)

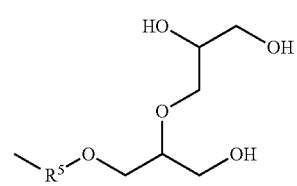

wherein $R^5$ is as defined above.

4. The co-modified organopolysiloxane according to claim 1, wherein, in General Formula (1), $R^1$ is a methyl group or a phenyl group, and $R^2$ is a halogen atom-substituted or unsubstituted alkyl group having 14 to 24 carbon atoms.

5. A surfactant or dispersing agent comprising the co-modified organopolysiloxane according to claim 1.

6. The surfactant or dispersing agent according to claim 5, wherein the surfactant or dispersing agent is used to prepare a composition having an oil agent as a continuous phase.

7. The surfactant according to claim 5, wherein the surfactant is an emulsifier for a water-in-oil emulsion.

8. A water-in-oil emulsion composition comprising the co-modified organopolysiloxane according to claim 1.

9. A water-in-oil emulsion composition comprising (S) the co-modified organopolysiloxane according to claim 1,
(T) water, and
(U) at least one oil agent that is liquid at 5 to 100° C. selected from the group consisting of silicone oils, non-polar organic compounds and lowly to highly polar organic compounds.

10. The water-in-oil emulsion composition according to claim 8, which does not comprise a compound having an oxyalkylene structure having an average number of repetitions of an oxyalkylene unit of two or higher.

11. An external use preparation or cosmetic composition comprising the co-modified organopolysiloxane according to claim 1.

12. An external use preparation or cosmetic composition comprising the water-in-oil emulsion composition according to claim 8.

13. The external use preparation or cosmetic composition according to claim 11, which is in the form of a water-in-oil emulsion.

14. The external use preparation or cosmetic composition according to claim 11, which does not comprise a compound having an oxyalkylene structure having an average number of repetitions of an oxyalkylene unit of two or higher.

* * * * *